(12) United States Patent
Hori et al.

(10) Patent No.: US 9,771,612 B2
(45) Date of Patent: Sep. 26, 2017

(54) METHOD FOR DETECTING A TARGET NUCLEIC ACID MOLECULE

(71) Applicant: OLYMPUS CORPORATION, Tokyo (JP)

(72) Inventors: Kunio Hori, Tokyo (JP); Kenzo Fujimoto, Kanazawa (JP)

(73) Assignee: OLYMPUS CORPORATION, Tokyo (JP)

( * ) Notice: Subject to any disclaimer, the term of this patent is extended or adjusted under 35 U.S.C. 154(b) by 172 days.

(21) Appl. No.: 14/486,030

(22) Filed: Sep. 15, 2014

(65) Prior Publication Data

US 2015/0004607 A1    Jan. 1, 2015

Related U.S. Application Data

(63) Continuation of application No. PCT/JP2013/053080, filed on Feb. 8, 2013.

(30) Foreign Application Priority Data

Mar. 21, 2012 (JP) ................................ 2012-063682

(51) Int. Cl.
| | | |
|---|---|---|
| C12Q 1/68 | (2006.01) | |
| C12P 19/34 | (2006.01) | |
| G01N 33/00 | (2006.01) | |
| C07H 21/02 | (2006.01) | |
| C07H 21/04 | (2006.01) | |
| G01N 21/64 | (2006.01) | |

(52) U.S. Cl.
CPC ......... *C12Q 1/6823* (2013.01); *C12Q 1/6816* (2013.01); *C12Q 1/6818* (2013.01); *G01N 21/6428* (2013.01); *G01N 2021/6441* (2013.01)

(58) Field of Classification Search
USPC ......... 435/6.1, 6.11, 91.1, 183; 436/94, 501; 536/23.1, 24.3, 24.33
See application file for complete search history.

(56) References Cited

U.S. PATENT DOCUMENTS

| | | | |
|---|---|---|---|
| 4,251,733 A | 2/1981 | Hirleman, Jr. | |
| 4,421,860 A | 12/1983 | Elings et al. | |
| 4,745,077 A | 5/1988 | Holian et al. | |
| 5,308,990 A | 5/1994 | Takahashi et al. | |
| 5,547,849 A | 8/1996 | Baer et al. | |
| 5,866,336 A | 2/1999 | Nazarenko et al. | |
| 6,280,960 B1 | 8/2001 | Carr | |
| 6,376,843 B1 | 4/2002 | Palo | |
| 6,388,746 B1 | 5/2002 | Eriksson et al. | |
| 6,388,788 B1 | 5/2002 | Harris et al. | |
| 6,400,487 B1 | 6/2002 | Harris et al. | |
| 6,403,338 B1 | 6/2002 | Knapp et al. | |
| 6,495,676 B1 | 12/2002 | Wood et al. | |
| 6,710,871 B1 | 3/2004 | Goix | |
| 6,782,297 B2 | 8/2004 | Tabor | |
| 6,856,391 B2 | 2/2005 | Garab et al. | |
| 6,927,401 B1 | 8/2005 | Palo | |
| 8,284,484 B2 | 10/2012 | Hoult et al. | |
| 2001/0035954 A1 | 11/2001 | Rahn et al. | |
| 2002/0008211 A1 | 1/2002 | Kask | |
| 2002/0036775 A1 | 3/2002 | Wolleschensky et al. | |
| 2003/0036855 A1 | 2/2003 | Harris et al. | |
| 2003/0218746 A1 | 11/2003 | Sampas | |
| 2004/0022684 A1 | 2/2004 | Heinze et al. | |
| 2004/0051051 A1 | 3/2004 | Kato et al. | |
| 2004/0150880 A1 | 8/2004 | Nakata et al. | |
| 2004/0152118 A1 | 8/2004 | Van Atta et al. | |
| 2005/0260660 A1 | 11/2005 | van Dongen et al. | |
| 2005/0277134 A1 | 12/2005 | Okano et al. | |
| 2006/0008799 A1 | 1/2006 | Cai et al. | |
| 2006/0078998 A1 | 4/2006 | Puskas et al. | |
| 2006/0158721 A1 | 7/2006 | Nakata et al. | |
| 2006/0256338 A1 | 11/2006 | Gratton et al. | |
| 2007/0070496 A1 | 3/2007 | Gweon et al. | |

(Continued)

FOREIGN PATENT DOCUMENTS

| | | |
|---|---|---|
| CN | 103620389 A | 3/2014 |
| EP | 1 906 172 A1 | 4/2008 |

(Continued)

OTHER PUBLICATIONS

Park, Mira et al., "Counting the Number of Fluorophores Labeled in Biomolecules by Observing the Fluorescence-Intensity Transient of a Single Molecule", Bulletin of the Chemical Society of Japan, Aug. 30, 2005, vol. 78, No. 9, p. 1612-1618.
U.S. Office Action dated Apr. 2, 2013, issued in related U.S. Appl. No. 13/596,280 (7 pages).
Kask, Peet et al., "Two-Dimensional Fluorescence Intensity Distribution Analysis: Theory and Applications", Biophysical Journal, Apr. 2000, vol. 78, p. 1703-1713.
International Search Report dated Mar. 29, 2011, issued in related PCT/JP2011/053483.

(Continued)

*Primary Examiner* — Frank Lu
(74) *Attorney, Agent, or Firm* — Westerman, Hattori, Daniels & Adrian, LLP

(57) ABSTRACT

A method for detecting a target nucleic acid comprising: forming a three-component association product by allowing the association of at least a nucleic acid molecule, a first nucleic acid probe having a first marker bound thereto, and a second nucleic acid probe having a second marker bound thereto; forming at least one covalent bond between the target nucleic acid molecule and the first nucleic acid probe and between the target nucleic acid molecule and the second nucleic acid probe; and binding the three-component association product to a solid phase carrier through the second marker; recovering the three-component association product bound to the solid phase carrier; releasing the first marker from the recovered three-component association product; and detecting the target nucleic acid molecule by detecting the free first marker.

11 Claims, 4 Drawing Sheets

(56) References Cited

U.S. PATENT DOCUMENTS

| | | | |
|---|---|---|---|
| 2007/0231808 | A1 | 10/2007 | Gouda et al. |
| 2008/0052009 | A1 | 2/2008 | Chiu et al. |
| 2008/0158561 | A1 | 7/2008 | Vacca et al. |
| 2009/0159812 | A1 | 6/2009 | Livingston |
| 2010/0033718 | A1 | 2/2010 | Tanaami |
| 2010/0177190 | A1 | 7/2010 | Chiang et al. |
| 2010/0202043 | A1 | 8/2010 | Ujike |
| 2010/0301231 | A1 | 12/2010 | Yamaguchi |
| 2010/0323350 | A1 | 12/2010 | Gordon et al. |
| 2011/0312841 | A1 | 12/2011 | Silverbrook et al. |
| 2013/0035871 | A1 | 2/2013 | Mayou et al. |
| 2014/0087482 | A1 | 3/2014 | Nishikawa |

FOREIGN PATENT DOCUMENTS

| | | |
|---|---|---|
| EP | 2216338 A1 | 8/2010 |
| EP | 2522988 A1 | 11/2012 |
| EP | 2543989 A1 | 1/2013 |
| EP | 2543990 A | 1/2013 |
| EP | 2584343 A1 | 4/2013 |
| EP | 2818850 A1 | 12/2014 |
| JP | 04501956 A | 4/1992 |
| JP | 04337446 A | 11/1992 |
| JP | 06113896 A | 4/1994 |
| JP | 2000-106876 A | 4/2000 |
| JP | 2002-507762 A | 3/2002 |
| JP | 2002-543414 A | 12/2002 |
| JP | 2004-506192 A | 2/2004 |
| JP | 2004-121231 A | 4/2004 |
| JP | 2004-187607 A | 7/2004 |
| JP | 2005-098876 A | 4/2005 |
| JP | 2005-099662 A | 4/2005 |
| JP | 2005-308412 A | 11/2005 |
| JP | 2006-333739 A | 12/2006 |
| JP | 2007-020565 A | 2/2007 |
| JP | 4023523 B | 12/2007 |
| JP | 2008-058285 A | 3/2008 |
| JP | 2008-116440 A | 5/2008 |
| JP | 2008-536093 A | 9/2008 |
| JP | 2008-292371 A | 12/2008 |
| JP | 2008-298743 A | 12/2008 |
| JP | 2009-145242 A | 7/2009 |
| JP | 2009-250721 A | 10/2009 |
| JP | 2009-281831 A | 12/2009 |
| JP | 2009-288161 A | 12/2009 |
| JP | 2010-019553 A | 1/2010 |
| JP | 2010-190730 A | 9/2010 |
| JP | 2011-002415 A | 1/2011 |
| JP | 2011-033613 A | 2/2011 |
| JP | 2011-036150 A | 2/2011 |
| JP | 2011-508219 A | 3/2011 |
| WO | 88/02785 A2 | 4/1988 |
| WO | 90/06042 A2 | 6/1990 |
| WO | 92/22671 A1 | 12/1992 |
| WO | 98/16814 A1 | 4/1998 |
| WO | 99/47963 A | 9/1999 |
| WO | 00/52451 A1 | 9/2000 |
| WO | 00/66985 A1 | 11/2000 |
| WO | 00/71991 A1 | 11/2000 |
| WO | 02/12864 A1 | 2/2002 |
| WO | 2004/020675 A2 | 3/2004 |
| WO | 2006/084283 A2 | 8/2006 |
| WO | 2007/010803 A1 | 1/2007 |
| WO | 2007/118209 A2 | 10/2007 |
| WO | 2007/147159 A2 | 12/2007 |
| WO | 2008/007580 A1 | 1/2008 |
| WO | 2008/080417 A1 | 7/2008 |
| WO | 2009/066447 A1 | 5/2009 |
| WO | 2009/117033 A2 | 9/2009 |
| WO | 2010/056579 A1 | 5/2010 |
| WO | 2011/108369 A1 | 9/2011 |
| WO | 2011/108370 A1 | 9/2011 |
| WO | 2011/108371 A1 | 9/2011 |
| WO | 2012/014778 A1 | 2/2012 |
| WO | 2012/144528 A1 | 10/2012 |

OTHER PUBLICATIONS

International Preliminary Report on Patentability (PCT/IPEA/409) issued in related PCT/JP2011/053483.

Chinese Office Action dated Aug. 9, 2013, issued in related Chinese application No. 201180011640.7; w/ English Translation (16 pages).

International Search Report Mar. 29, 2011, issued in related PCT/JP2011/053482.

International Preliminary Report on Patentability (PCT/IPEA/409) issued in related PCT/JP2011/053482.

Sasaki, Shigeki, "Creation of Functional Recognition Molecules for Chemical Modification of Gene Expression", Yakugaku Zasshi, the Pharmaceutical Society of Japan, 2002, vol. 122, No. 12, p. 1081-1093.

Chinese Office Action dated Feb. 7, 2013, issued in related Chinese application No. 201180011644.5; w/ English Translation (19 pages).

Extended European Search Report dated Mar. 28, 2013, issued in related EP application No. 11750481.1.

International Search Report dated Mar. 29, 2011, issued in related PCT/JP2011/053481.

International Preliminary Report on Patentability (PCT/IPEA/409) issued in related PCT/JP2011/053481.

Goodwin, Peter et al., "Rapid Sizing of Individual Fluorescently Stained DNA Fragments by Flow Cytometry", Nucleic Acids Research, 1993, vol. 21, No. 4, p. 803-806.

Keller, Richard et al., "Single-Molecule Fluorescence Analysis in Solution", Applied Spectroscopy, 1996, vol. 50, No. 7, p. 12A-32A.

Lee, Yuan-Hsiang et al., "Laser-Induced Fluorescence Detection of a Single Molecule in a Capillary", Analytical Chemistry, Dec. 1, 1994, vol. 66, No. 23, p. 4142-4149.

Li, Haitao et al., "Ultrasensitive Coincidence Fluorescence Detection of Single DNA Molecules", Analytical Chemistry, Apr. 1, 2003, vol. 75, No. 7, p. 1664-1670.

Nie, Shuming et al., "Probing Individual Molecules with Confocal Fluorescence Microscopy", Science, Nov. 11, 1994, vol. 266, p. 1018-1021.

Tahari, Abdel. "Fluorescence Correlation Spectroscopy: Ultrasensitive Detection in Clear and Turbid Media", University of Illinois, 2006, p. 1-88.

Wu, Alan et al., "Development and Preliminary Clinical Validation of a High Sensitivity Assay for Cardiac Troponin Using a Capillary Flow (Single Molecule) Fluorescence Detector", Clinical Chemistry, 2006, vol. 52, No. 11, p. 2157-2159.

Carlsson, K. et al., "Three-dimensional Microscopy Using a Confocal Laser Scanning Microscope", Optics Letters, Optical Society of America, Feb. 1985, vol. 10, No. 2, p. 53-55, X007922413.

U.S. Office Action dated Oct. 4, 2013, issued in related U.S. Appl. No. 13/596,243 (7 pages).

Japanese Office Action dated Dec. 18, 2012, issued in related JP application No. 2012-503060; w/ English Translation (6 pages).

Yoshimura, Yoshinaga et al., "Development of Template-Directed Reversible DNA Photocrosslinking", Nucleic Acids Symposium Series, 2008, vol. 10, No. 52, p. 423-424.

Yoshimura, Yoshinaga et al., "Ultrafast Reversible Photo-Cross-Linking Reaction: Toward in Situ DNA Manipulation", Organic Letters, 2008, vol. 10, No. 15, p. 3227-3230.

Takasugi, M. et al., "Sequence-Specific Photo-Induced Cross-Linking of the Two Strands of Double-Helical DNA by a Psoralen Covalently Linked to a Triple Helix-Forming Oligonucleotide", Proc. Natl. Acad. Sci. USA, Jul. 1991, vol. 88, p. 5602-5606.

Kask, Peet et al. "Fluorescence-Intensity Distribution Analysis and its Application in Biomolecular Detection Technology", PNAS, Nov. 23, 1999, vol. 96, No. 24, p. 13756-13761.

Kinjo, M. "Single Molecule Detection by Fluorescence Correlation Spectroscopy", Proteins, Nucleic Acids and Enzymes, 1999, vol. 44, No. 9, p. 1431-1438.

Meyer-Almes, F. J. "A New Method for Use in Molecular Diagnostics and High Throughput Pharmaceutical Screening based on Fluorescence Correlation Spectroscopy", Nanoparticle Immunoassays, R. Ridger, edit., Springer, Berlin, 2000, p. 204-224.

(56) References Cited

OTHER PUBLICATIONS

Kato, N. et al., "A Single Molecule Analyzer that Enables New Analysis of DNA and Protein Interactions", Gene Medicine, 2002, vol. 6, No. 2, p. 271-277 with partial translation.
Sando, Shinsuke et al., "Quencher as Leaving Group: Efficient Detection of DNA-Joining Reactions", Journal of the American Chemical Society, 2002, vol. 124, No. 10, p. 2096-2097.
International Search Report dated Sep. 20, 2011, issued in related PCT/JP2011/066576 (6 pages).
U.S. Office Action dated Feb. 20, 2014, issued in related U.S. Appl. No. 13/746,968 (11 pages).
U.S. Notice of Allowance dated Mar. 27, 2013, issued in related U.S. Appl. No. 13/597,825 (8 pages).
U.S. Office Action dated May 22, 2014, issued in related U.S. Appl. No. 13/746,968 (10 pages).
International Search Report dated Apr. 23, 2013, issued in related PCT/JP2013/053080 (4 pages).
International Search Report dated Jul. 24, 2012, issued in related PCT/JP2012/060137 (6 pages).
International Search Report dated Mar. 5, 2013, issued in related PCT/JP2013/081350 (2 pages).
Chinese Office Action dated Jul. 14, 2014, issued in related Chinese application No. 201180036710.4; w/ English Translation (12 pages).
European Official Communication dated Nov. 20, 2014, issued in related EP Application No. 11812369.4 (5 pages).
Shuming N. et al., "Real-Time Detection of Single Molecules in Solution by Confocal Fluorescence Microscopy", Analytical Chemistry, American Chemical Society, vol. 67, No. 17, pp. 2849-2857, (1995), cited in European Official Communication dated Nov. 20, 2014 (9 pages).
Extended European Search Report issued Feb. 16, 2016 in EP 13764425.8.
U.S. Office Action dated Apr. 13, 2015, issued in U.S. Appl. No. 13/746,968 (19 pages).
Extended European Search Report dated Oct. 20, 2014, issued in related EP Application No. 12770835.2 (10 pages).
U.S. Non-Final Office Action dated Mar. 4, 2015, issued in U.S. Appl. No. 14/172,295 (39 pages).
Office Action dated Mar. 25, 2015, issued in Chinese Patent Application No. 201180036710.4, with English translation (8 pages).
Notice of Reasons for Rejection dated May 19, 2015, issued in corresponding Japanese Patent Application No. 2012-526460 with English translation (8 pages).
Hebert et al., "Spatiotemporal Image Correlation Spectroscopy (STICS) Theory, Verification, and Application to Protein Velocity Mapping in Living CHO Cells", Biophysical Journal, May 2005, vol. 88, No. 5, pp. 3601-3614, cited in Extended European Search Report dated Mar. 26, 2015 (14 pages).
Extended European Search Report dated Mar. 26, 2015, issued in corresponding EP Patent Application No. 12821897.1 (13 pages).
Itoh et al., "A New Method for Detection of Influenza Viruses by Single Particle-Recognition Based on the Principle of Fluorescence Correlation Spectroscopy", Chemistry and Biology, 2009, vol. 47, No. 12, p. 823-830 with English concise explanation (9 pages).
Non-Final Office Action dated Aug. 20, 2015, issued in U.S. Appl. No. 14/172,295 (22 pages).
Non-Final Office Action dated Sep. 28, 2015, issued in U.S. Appl. No. 14/322,010. (10 pages).
Final Office Action dated Sep. 28, 2015, issued in U.S. Appl. No. 13/746,968 (24 pages).
Office Action dated Apr. 20, 2015, issued in Chinese Patent Application No. 201280041270.6 with English translation (11 pages).
Extended European Search Report dated May 20, 2015, issued in European Patent Application No. 12828423.9 (18 pages).
Communication pursuant to Article 94(3) dated May 13, 2015, issued in European Patent Application No. 11 812 369.4 (5 pages).
Advisory Action mailed Jan. 5, 2016, issued in U.S. Appl. No. 14/172,295.
Advisory Action mailed Feb. 2, 2016, issued in U.S. Appl. No. 13/746,968.
Official Notice dated Nov. 30, 2015, issued in European application No. 11812369.4.
Prasad V et al. "Topical Review; Confocal microscopy of colloids", Journal of Physics: Condensed Matter, Institute of Physics Publishing, Bristol, GB, vol. 19, No. 11, Mar. 21, 2007, p. 113102.
Smoothing, Wikipedia Online entry at http://web.archive.org/web/20110226071633/http://en.wikipedia.org/wiki, Smoothing.
Office Action dated Feb. 22, 2017, issued in European Application No. 12828423.9. (6 pages).
Enderlein, Jorg et al., "Optimal Algorithm for Single-Molecule Identification with Time-Correlated Single-Photon Counting", J. Phys. Chem. A, 2001, vol. 105, pp. 48-53.
Yan, Yuan et al., "Simultaneous Enantiomeric Determination of Dansyl-D, L-Phenylalanine by Fluorescence Spectroscopy in the Presence of a-Acid Glycoprotein", Anal. Chem., 1999, vol. 71, pp. 1958-1962.
Final Office Action dated Apr. 21, 2017, issued in U.S. Appl. No. 14/179,174 (18 pages).
Non-Final Office Action dated Oct. 24, 2016, issued in related U.S. Appl. No. 14/179,174 (63 pages).
Chinese Office Action dated Aug. 13, 2013, issued in related Chinese application No. 201180011655.3; w/ English Translation (16 pages).
International Search Report dated Aug. 7, 2012, issued in related PCT/JP2012/066576 (4 pages).

SEQUENCE LISTING

```
<160> NUMBER OF SEQ ID NOS: 5

<210> SEQ ID NO 1
<211> LENGTH: 22
<212> TYPE: RNA
<213> ORGANISM: Homo sapiens
<220> FEATURE:
<223> OTHER INFORMATION: Description of Artificial Sequence: cDNA of
      human let-7a.

<400> SEQUENCE: 1
ugagguagua gguuguauag uu                                              22

<210> SEQ ID NO 2
<211> LENGTH: 9
```

```
<212> TYPE: DNA
<213> ORGANISM: Artificial Sequence
<220> FEATURE:
<223> OTHER INFORMATION: Description of Artificial Sequence: The only
      5th nucleic acid is different  from 7a right tamra-1 probe.

<400> SEQUENCE: 2 actacctca                                                                 9

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: The only
      16th nucleic acid is different  from B-7aL1 probe.

<400> SEQUENCE: 3
tttttttttt aactatacaa cct                                                23

<210> SEQ ID NO 4
<211> LENGTH: 9
<212> TYPE: DNA
<213> ORGANISM: Artificial Sequence
<220> FEATURE:
<223> OTHER INFORMATION: 7a right tamra-1 probe

<400> SEQUENCE: 4 actakctca                                                                 9

<210> SEQ ID NO 5
<211> LENGTH: 23
<212> TYPE: DNA
<213> ORGANISM: Artificial Sequence
<220> FEATURE:
<223> OTHER INFORMATION: B-7aL1 probe.

<400> SEQUENCE: 5
tttttttttt aactakacaa cct                                                23
```

METHOD FOR DETECTING A TARGET NUCLEIC ACID MOLECULE

The present application is a U.S. continuation application based on the PCT International Patent Application, PCT/JP2013/053080, filed on Feb. 8, 2013; the contents of which are incorporated herein by reference.

BACKGROUND OF THE INVENTION

Field of the Invention

The present invention relates to a method for detecting a target nucleic acid molecule using a photocrosslinking reaction.

The present application claims priority on the basis of Japanese Patent Application No. 2012-063682, filed in Japan on Mar. 21, 2012, the contents of which are incorporated herein by reference.

Description of the Related Art

Nucleic acid molecules in a sample solution can be detected by a hybridization method using a labeled probe that specifically hybridizes with the nucleic acid molecule. As an example of a method thereof, after hybridizing a labeling probe preliminarily immobilized on beads with a target nucleic acid molecule, the nucleic acid molecule that has been hybridized and immobilized on the beads is precipitated on the bottom of a container. The temperature of the reaction liquid is subsequently gradually raised to a temperature equal to or higher than the denaturation temperature of the target nucleic acid to release the labeling probe from the beads into the supernatant followed by measuring the amount of light or fluorescence in the supernatant over time (see, for example, Japanese Unexamined Patent Application, First Publication No. 2004-121231).

In addition, a method has been disclosed that consists of introducing a reactive functional group into a base that composes an oligonucleotide, and forming covalent bonds between other oligonucleotides and other molecules through this reactive functional group (crosslinking). For example, examples of technologies for crosslinking nucleic acid molecules by covalent bonding using a base derivative introduced with a reactive functional group include a method that uses 2-amino-6-vinylpurine (see, for example, Sasaki, S., Yakugaku Zasshi, 2002, Vol. 122, No. 12, pp. 1081-1093), and a method that uses a photoreactive base derivative in the form of 3-cyanovinylcarbazole nucleoside (see, for example, Fujimoto, et al., Nucleic Acids Symposium Series, 2008, Vol. 52, pp. 423-424; Yoshimura, et al., Organic Letters, 2008, Vol. 10, No. 15, pp. 3227-3230; International Publication No. WO 09/066,447).

Other methods consist of quantifying a nucleic acid molecule by using a photocrosslinking reaction and fluorescence resonance energy transfer (FRET). For example, a method has been disclosed that consists of associating a FRET probe and target nucleic acid molecule under conditions suitable for specific association followed by forming covalent bonds by using a photocrosslinking reaction between the two nucleic acid strands of the association product formed without changing the temperature or salt concentration of the reaction solution, and then detecting and analyzing this association product for each molecule thereof (see, for example, Japanese Unexamined Patent Application, First Publication No. 2011-036150). In the case of detecting using hybridization, although there is increased susceptibility to the formation of non-specific association products (association products formed by non-specific hybridization) during the association product detection procedure since detection of the association product formed is typically carried out under ordinary measurement temperature conditions (such as room temperature), in the case of the previously described method, the formation of non-specific association products can be effectively suppressed due to stabilization of the association product formed between the FRET probe and target nucleic acid molecule by a photocrosslinking reaction.

A FRET probe that specifically binds to a specific nucleic acid molecule is also used to detect antigen-antibody reactions. For example, a method has been disclosed that consists of carrying out an antigen-antibody reaction using an antibody labeled with single-stranded DNA and binding the antigen-antibody complex formed with a FRET probe complementary to the single-stranded DNA used to label the antibody, followed by releasing the fluorescent substance in the FRET probe from the antigen-antibody complex into the reaction liquid supernatant by treating with a nucleolytic enzyme, and detecting the antigen by measuring fluorescence intensity of the reaction liquid supernatant (see, for example, Japanese Unexamined Patent Application, First Publication No. 2011-033613).

SUMMARY OF THE INVENTION

As a result of conducting extensive studies to solve the aforementioned problems, it was found that, after having hybridized a target nucleic acid molecule with both a labeling probe labeled with a luminescent substance and a probe that mediates binding with a solid phase carrier, and separated from free labeling probe and recovered the resulting three-component association product while bound to the solid phase carrier; by separating the luminescent substance in the aforementioned association product from the solid phase carrier and detecting the luminescent substance in the free state, the target nucleic acid molecule can be detected with high accuracy and without being affected by the solid phase carrier. Moreover, it was also found that, by stabilizing the resulting three-component association product by covalent bonding prior to separating and recovering free labeling probe, target nucleic acid molecules in a sample can be detected with even higher accuracy.

Namely, several aspects of the present invention provide that indicated below.

(1) A method for detecting a target nucleic acid molecule in one aspect of the present invention has:

(a) preparing a sample solution obtained by adding a nucleic acid-containing sample, a first nucleic acid probe that has a luminescent substance in the form of a first marker bound thereto and specifically hybridizes with the target nucleic acid molecule, and a second nucleic acid probe that has a second marker bound thereto and specifically hybridizes with a target nucleic acid molecule in a region that differs from the region hybridized by the first nucleic acid probe;

(b) denaturing the nucleic acid molecule in the sample solution prepared in the (a);

(c) allowing the nucleic acid molecules in the sample solution to associate after the (b);

(d) forming at least one covalent bond between the target nucleic acid molecule and the first nucleic acid probe and forming at least one covalent bond between the target nucleic acid molecule and the second nucleic acid probe in the three-component association product formed in the (c) composed of the target nucleic acid molecule, the first nucleic acid probe and the second nucleic acid probe;

(e) adding, after the (d), a solid phase carrier provided with a site that binds with the second marker to the sample solution, binding the solid phase carrier and the three-component association product through the second marker in the three-component association product, and recovering the three-component association product bound to the solid phase carrier by solid-liquid separation treatment;

(f) releasing the first marker from the recovered three-component association product after the (e); and, (g) detecting the target nucleic acid molecule by detecting the free first marker after the (f).

(2) In the aforementioned (f) of the method for detecting a target nucleic acid molecule described in (1) above, the first marker is released from the three-component association product by:

(f1) irradiating the three-component association product with ultraviolet light at 300 nm to 380 nm under conditions in which the three-component association product dissociates in the case a covalent bond is not formed between the target nucleic acid molecule and the first nucleic acid probe or between the target nucleic acid molecule and the second nucleic acid probe;

(f2) decomposing the three-component association product with a nucleolytic enzyme;

(f3) heating the three-component association product to 80° C. or higher; or, (f4) heating the three-component association product to 50° C. to 100° C. under alkaline conditions.

(3) In (f1) above of the method for detecting a target nucleic acid molecule described in (2) above, irradiation of the three-component association product with ultraviolet light is carried out in a solution containing a salt at a concentration at which the Tm value of the first nucleic acid probe is 25° C. or lower.

(4) In the method for detecting a target nucleic acid molecule described in any of (1) to (3) above, a reaction for forming the covalent bond is a photochemical reaction mediated by a photoreactive base derivative.

(5) In the method for detecting a target nucleic acid molecule described in (4) above, at least one base in a region of the first nucleic acid probe that hybridizes with the target nucleic acid molecule is substituted with a photoreactive base derivative, and at least one base in a region of the second nucleic acid probe that hybridizes with the target nucleic acid molecule may be substituted with a photoreactive base derivative.

(6) In the method for detecting a target nucleic acid molecule described in (4) or (5) above, the photoreactive base derivative is 3-cyanovinylcarbazole nucleoside, and the covalent bond is formed by irradiating the sample solution with light at 340 nm to 380 nm.

(7) In the method for detecting a target nucleic acid molecule described in any of (1) to (6) above, prior to the (f), the three-component association product bound to the solid phase carrier recovered in the (e) is washed with a washing solution having a salt concentration at which the Tm value of the first nucleic acid probe is 25° C. or lower.

(8) In the (g) of the method for detecting a target nucleic acid molecule described in any of (1) to (7) above, the detecting of the first marker is carried out using a fluorescent single molecule measurement method.

(9) In the (g) of the method for detecting a target nucleic acid molecule described in (8) above, the detecting of the first marker is carried out by:

(p) calculating the number of molecules of the first marker present in a measurement solution containing the free first marker by fluorescence correlation spectroscopy or fluorescence intensity distribution analysis, or (r) moving the location of a photodetection region of an optical system of a confocal microscope or multi-photon microscope in a measurement solution containing the free first marker while detecting light from the photodetection region using the optical system, thereby calculating the number of molecules of the first marker present in the measurement solution.

(10) In the method for detecting a target nucleic acid molecule described in any of (1) to (9) above, the (a) is:

(a') preparing a sample solution by adding the nucleic acid-containing sample, the first nucleic acid probe, the second nucleic acid probe, and a solid phase carrier provided with a site that binds with the second marker; and the (e) is:

(e') recovering the three-component association product by subjecting the sample solution to solid-liquid separation treatment after the (d).

(11) In the method for detecting a target nucleic acid molecule described in (10) above, the (a') is:

(a") preparing a sample solution by adding the nucleic acid-containing sample, the first nucleic acid probe, and the second nucleic acid probe bound to a solid phase carrier.

(12) Another aspect of the present invention is a target nucleic acid molecule detection kit used in the method for detecting a target nucleic acid molecule described in any of (1) to (11) above, including:

a first nucleic acid to which a first marker, that is a luminescent substance, is bound, and which specifically hybridizes with a target nucleic acid molecule, and a second nucleic acid probe to which a second marker is bound, and which specifically hybridizes with a target nucleic acid molecule in a region that differs from the region hybridized by the first nucleic acid probe.

(13) In the target nucleic acid molecule detection kit described in (12) above, at least one base in a region of the first nucleic acid probe that hybridizes with the target nucleic acid molecule is substituted with a photoreactive base derivative, and at least one base in a region of the second nucleic acid probe that hybridizes with the target nucleic acid molecule may be substituted with a photoreactive base derivative.

(14) In the target nucleic acid molecule detection kit described in (12) or (13) above, a solid phase carrier provided with a site that binds with the second marker may be further included.

DESCRIPTION OF THE PREFERRED EMBODIMENTS

Figure 1:
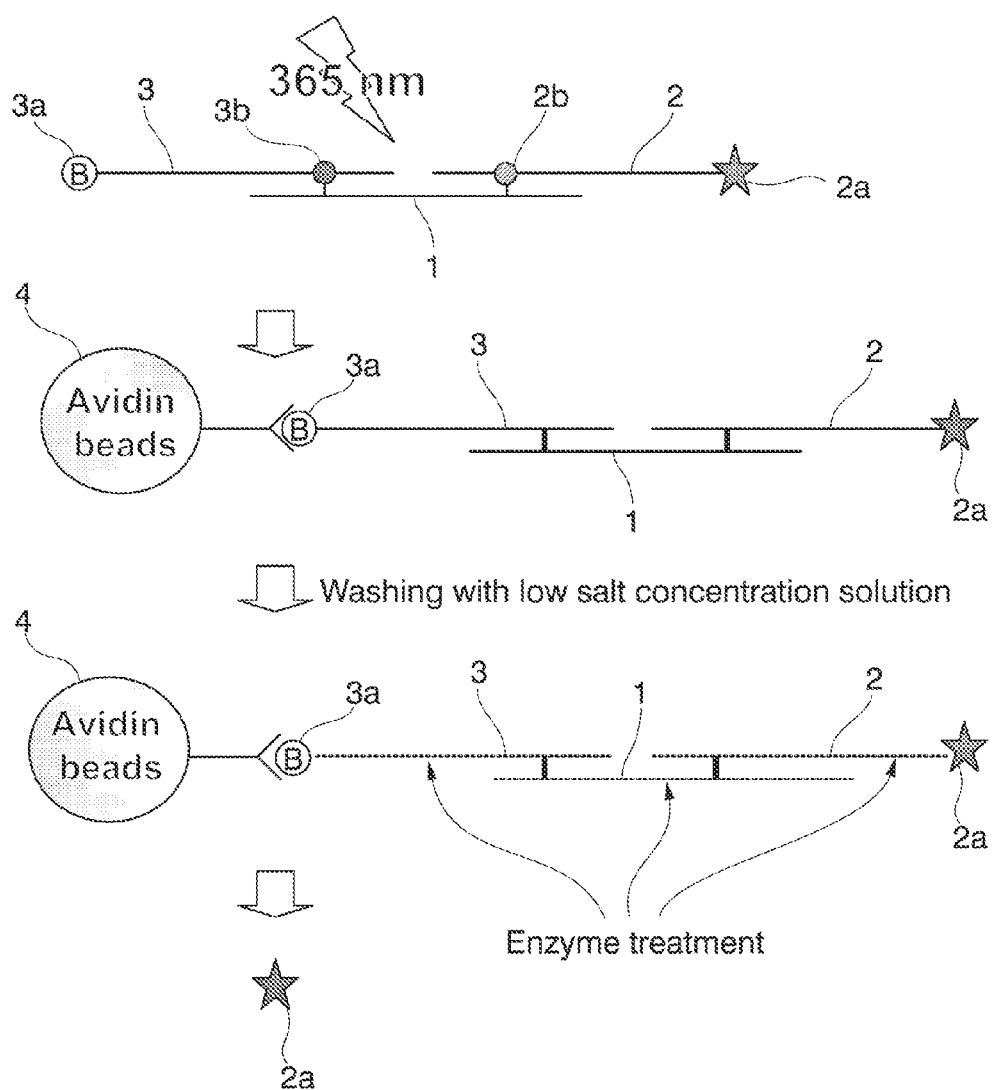
FIG. 1 is a drawing schematically showing one aspect of the method for detecting a target nucleic acid molecule of the present invention.

The method for detecting a target nucleic acid molecule in one aspect of the present invention has the following operations (a) to (g):

(a) preparing a sample solution obtained by adding a nucleic acid-containing sample, a first nucleic acid probe that has a luminescent substance in the form of a first marker bound thereto and specifically hybridizes with a target nucleic acid molecule, and a second nucleic acid probe that has a second marker bound thereto and specifically hybridizes with a target nucleic acid molecule in a region that differs from the region hybridized by the first nucleic acid probe;

(b) denaturing the nucleic acid molecule in the sample solution prepared in the (a);

(c) allowing the nucleic acid molecules in the sample solution to associate after the (b);

(d) forming at least one covalent bond between the target nucleic acid molecule and the first nucleic acid probe and forming at least one covalent bond between the target nucleic acid molecule and the second nucleic acid probe in a three-component association product formed in the (c) composed of the target nucleic acid molecule, the first nucleic acid probe and the second nucleic acid probe;

(e) adding a solid phase carrier provided with a site that binds with the second marker to the sample solution after the (d), and binding the solid phase carrier and the three-component association product through the second marker in the three-component association product, followed by recovering the three-component association product bound to the solid phase carrier by solid-liquid separation treatment;

(f) releasing the first marker from the recovered three-component association product after the (e); and, (g) detecting the target nucleic acid molecule by detecting the free first marker after the (f).

In the present embodiment, a target nucleic acid molecule refers to a nucleic acid molecule having a specific base sequence that is a target of detection. There are no particular limitations on the aforementioned target nucleic acid molecule provided the base sequence has been clearly determined to a degree that enables the design of a nucleic acid probe that specifically hybridizes with the nucleic acid molecule. For example, the target nucleic acid molecule may be a nucleic acid molecule having a base sequence present in the chromosome of an animal or plant or gene of a bacterium or virus, or a nucleic acid molecule having an artificially designed base sequence. Furthermore, in the present embodiment, the target nucleic acid molecule may be a double-stranded nucleic acid or single-stranded nucleic acid. In addition, it may be DNA or RNA. Examples of the aforementioned target nucleic acid molecule include micro-RNA, siRNA, mRNA, hnRNA, genomic DNA, synthetic DNA obtained by PCR or other amplification and cDNA synthesized from RNA using a reverse transcriptase.

In addition, in the present embodiment, there are no particular limitations on the nucleic acid-containing sample provided it is a sample that contains a nucleic acid molecule. Examples of the aforementioned nucleic acid-containing sample include biological samples collected from animals and the like, samples prepared from cultured cells and the like, and reaction solutions following a nucleic acid synthesis reaction. A biological sample may be used as is for the nucleic acid-containing sample, or the nucleic acid-containing sample may be a nucleic acid solution that has been extracted or purified from a biological sample and the like.

In the present embodiment, a "nucleic acid probe that specifically hybridizes with a target nucleic acid molecule" refers to that which is only required to be a nucleic acid probe that preferentially hybridizes with a target nucleic acid molecule rather than binding to another nucleic acid molecule having a similar base sequence with that the target nucleic acid molecule, and is not required to not hybridize at all with nucleic acid molecules other than the target nucleic acid molecule. For example, the nucleic acid probe that specifically hybridizes with a target nucleic acid molecule may be an oligonucleotide having a base sequence completely complementary to a partial base sequence of the target nucleic acid molecule, or may have a base sequence that contains one to several base mismatches with a partial base sequence of the target nucleic acid molecule.

The first nucleic acid probe used in the present embodiment has a first marker bound thereto and specifically hybridizes with a target nucleic acid molecule. Examples of the first nucleic acid probe include an oligonucleotide that has a base sequence completely complementary to a partial base sequence of a target nucleic acid molecule or a base sequence having one to several base mismatches with that partial base sequence, and has the first marker bound thereto.

The first marker is a luminescent substance. Examples of luminescent substances include particles that emit light by fluorescence, phosphorescence, chemiluminescence, bioluminescence or light scattering (and are normally molecules or aggregates thereof). In the present embodiment, a fluorescent substance may be used for the first marker due to high detection sensitivity. There are no particular limitations on the fluorescent substance provided it is a substance that releases fluorescent light as a result of being irradiated with light of a specific wavelength, and can be suitably selected and used from among fluorescent dyes, quantum dots and the like used in optical analyses such as FCS or FIDA.

The second nucleic acid probe used in the present embodiment has a second marker bound thereto and specifically hybridizes with a target nucleic acid molecule. Examples of the second nucleic acid probe include an oligonucleotide that has a base sequence completely complementary to a partial base sequence of a target nucleic acid molecule or a base sequence having one to several base mismatches with that partial base sequence, and has the second marker bound thereto.

There are no particular limitations on the second marker provided it is a substance that can be detected by being distinguished from the first marker. For example, the second marker may be a non-luminescent substance or a luminescent substance that has luminescence properties differing from those of the first marker. Furthermore, different luminescent properties refer to differences in light intensity at a specific wavelength (such as having different fluorescence intensity at a specific wavelength).

Examples of the second marker include fluorescent substances having different luminescence properties from those of the first marker, nucleic acids (oligonucleotides), hydrophilic organic compounds, biotin, glutathione, dinitrophenol (DNP), digoxigenin (Dig), digoxin, sugar chains composed of two or more sugars, polypeptides composed of six or more amino acids, auxins, gibberellins, steroids, proteins and analogs thereof.

An oligonucleotide composing the first nucleic acid probe or second nucleic acid probe may be DNA or RNA, may be artificially amplified in the manner of cDNA, or may contain all or a portion of a nucleic acid-like substance capable of forming a nucleotide chain and base pairs in the same manner as naturally-occurring nucleic acid bases. Examples of nucleic acid-like substances include substances in which side chains and the like of naturally-occurring nucleotides (nucleotides present in nature) in the manner of DNA or RNA have been modified by functional groups such as an amino group, and substances that have been labeled with a protein or low molecular weight compound and the like. Specific examples of nucleic acid-like substances include bridged nucleic acids (BNA), nucleotides in which an oxygen atom at position 4' of a naturally-occurring nucleotide has been substituted with a sulfur atom, nucleotides in which a hydroxyl group at position 2' of a naturally-occurring nucleotide has been substituted with a methoxy group, hexitol nucleic acids (HNA) and peptide nucleic acids (PNA).

An oligonucleotide that composes the first nucleic acid probe or the second nucleic acid probe may have a region other than the region that hybridizes with the target nucleic acid molecule. For example, a region that hybridizes with a target nucleic acid molecule and a region that binds the first marker or the second marker may be linked with a linker having a suitable base length.

The first nucleic acid probe or the second nucleic acid probe can be produced by designing a base sequence based on base sequence information of a target nucleic acid molecule or base sequence information of a region that forms a base pair, and binding a marker to the nucleic acid probe synthesized based on that design. A marker may also be bound simultaneous to synthesis of the nucleic acid probe. Design and synthesis of the first nucleic acid probe or the second nucleic acid probe, a binding reaction between the first nucleic acid probe and the first marker, and a binding reaction between the second nucleic acid probe and a second marker can be carried out according to ordinary methods.

Both the first nucleic acid probe and the second nucleic acid probe hybridize with a single target nucleic acid molecule, and a three-component association product is formed that is composed thereof. Namely, a region that hybridizes with the first nucleic acid probe and a region that hybridizes with the second nucleic acid probe in a target nucleic acid molecule are mutually different. In the case the target nucleic acid molecule is a double-stranded nucleic acid molecule, both the first nucleic acid probe and the second nucleic acid probe hybridize with a single-stranded nucleic acid molecule thereof. Furthermore, the first nucleic acid probe and the second nucleic acid probe may hybridize simultaneously with a target nucleic acid molecule.

Conditions for specific association between the first nucleic acid probe and a target nucleic acid molecule and conditions for specific association between the second nucleic acid probe and a target nucleic acid molecule may be nearly the same conditions in order to allow the first nucleic acid probe and the second nucleic acid probe to hybridize with a single target nucleic acid molecule. The specific association conditions are dependent on such factors as the types and lengths of the base sequences of the target nucleic acid molecule and nucleic acid probes.

Accordingly, the first nucleic acid probe and the second nucleic acid probe may be designed so as to satisfy specific association conditions.

More specifically, specific association conditions between a target nucleic acid molecule and the nucleic acid probes can be determined from a melting curve. Since the formation of an association product is typically dependent on temperature conditions and salt concentration conditions, a melting curve can be determined by changing the temperature of a solution containing only a nucleic acid probe and a target nucleic acid molecule from a high temperature to a low temperature and measuring optical absorbance of the aforementioned solution. Temperature conditions over a range from the temperature at which a nucleic acid probe present in the form of a single strand begins to form an association product with a target nucleic acid molecule to the temperature at which nearly all have formed an association product as determined from the resulting melting curve can be taken to be the specific association conditions. Specific association conditions can also be determined by similarly determining a melting curve by changing the salt concentration in the solution from a low concentration to a high concentration instead of changing temperature.

In this manner, although specific association conditions differ for each type of target nucleic acid molecule and nucleic acid probe and are determined experimentally, the Tm value (melting temperature) can generally be used instead.

For example, the Tm value of a region having a base sequence complementary to a target nucleic acid molecule (temperature at which 50% of double-stranded DNA dissociates to single-stranded DNA) can be calculated from base sequence information of a nucleic acid probe by using commonly used primer/probe design software and the like. Conditions in which the temperature is in the vicinity of the Tm value, and for example, conditions in which the temperature is within about ±3° C. of the Tm value, can be used as specific association conditions. More detailed specific association conditions can be determined by experimentally determining a melting curve at a temperature in the vicinity of the calculated Tm value.

First, in (a), a sample solution is prepared by adding a nucleic acid-containing sample, a first nucleic acid probe and a second nucleic acid probe to a suitable solvent. There are no particular limitations on the aforementioned solvent provided it is a solvent that does not damage the first marker or second marker, and can be suitably selected and used from among buffers commonly used in the art. Examples of such buffers include phosphate buffers and Tris buffers, such as phosphate-buffered saline (PBS, pH 7.4). In addition, an organic solvent such as formamide may also be used depending on the type of first marker and second marker.

Next, in (b), nucleic acid molecules in the prepared sample solution are denatured. In the present embodiment, denaturing of nucleic acid molecules refers to the dissociation of base pairs. For example, this refers to converting a double-stranded nucleic acid to a single-stranded nucleic acid. In the present embodiment, since there is comparatively little effect on luminescent substances such as fluorescent substances, denaturation by high-temperature treatment (heat denaturation) or denaturation by low salt concentration treatment can be carried out. Heat denaturation is a simple procedure. Nucleic acid molecules in a sample solution can be denatured by subjecting the sample solution to high-temperature treatment. In general, although nucleic acid molecules can be denatured by incubating at a temperature of 90° C. for DNA or 70° C. for RNA for several seconds to about 2 minutes, since the denaturation temperature varies according to the base length of the target nucleic acid molecule, the aforementioned incubation temperature is not limited thereto provided denaturation is possible. On the other hand, denaturation by low salt concentration treatment can be carried out by, for example, adjusting the salt concentration of the sample solution to be sufficiently low by diluting with purified water and the like.

Next, in (c), nucleic acid molecules in the aforementioned sample solution are allowed to associate. Formation of an association product of a target nucleic acid molecule, first nucleic acid probe and second nucleic acid probe is carried out under specific association conditions. More specifically, in the case of having carried out heat denaturation, nucleic acid molecules in the aforementioned sample solution are allowed to suitably associate by lowering the temperature of the sample solution to a temperature that satisfies specific association conditions after high-temperature treatment. The temperature of the sample solution can be lowered to a temperature that is within about ±3° C. of the Tm value of a region in the first nucleic acid probe and second nucleic acid probe having a base sequence complementary to the target nucleic acid molecule. On the other hand, even in the case of having carried out denaturation by low salt concentration treatment as well, nucleic acid molecules in the sample solution are allowed to suitably associate by similarly raising the salt concentration of the sample solution to a concentration that satisfies specific association conditions by adding a salt solution and the like after low salt concentration treatment.

In order to suppress non-specific hybridization, the temperature of the solution can be lowered comparatively slowly when forming an association product. For example, after having denatured a nucleic acid molecule by making the temperature of the solution to be 70° C. or higher, the liquid temperature of the solution can be lowered at a temperature lowering rate of 0.05° C./second or higher.

In addition, in order to suppress non-specific hybridization, a surfactant, formamide, dimethylsulfoxide or urea and the like may be added to the aforementioned solution in advance.

Only one type of these compounds may be added or two or more types may be added in combination. The addition of these compounds makes it possible to make it difficult for non-specific hybridization to occur in a comparatively low-temperature environment.

Subsequently, in (d), at least one covalent bond is formed between the target nucleic acid molecule and the first nucleic acid probe and at least one covalent bond is formed between the target nucleic acid molecule and the second nucleic acid probe in the three-component association product formed in the (c) composed of the target nucleic acid molecule, the first nucleic acid probe and the second nucleic acid probe. As a result of respectively forming covalent bonds between the target nucleic acid molecule and each of the nucleic acid probes, the three-component association product consisting of the target nucleic acid molecule, the first nucleic acid probe and the second nucleic acid probe can be stabilized even in a state in which temperature is not controlled to so-called normal temperature.

There are no particular limitations on the method used to form covalent bonds in (d) provided it enables the formation of covalent bonds that link two single-stranded nucleic acids forming base pairs, and can be suitably selected and carried out from among known techniques used when crosslinking nucleic acid molecules.

Furthermore, formation of covalent bonds in (d) may be carried out in a state in which the three-component association product formed in (c) is maintained. For example, in the case of having formed the three-component association product in (c) by lowering the temperature of the sample solution to a temperature that allows formation of the three-component association product, formation of covalent bonds in (d) may be carried out without changing the temperature of the sample solution.

Furthermore, although the same conditions as those during formation of the three-component association product in (c) may be the conditions under which the temperature and salt concentration of the sample solution are mutually the same, the conditions are not necessarily required to be completely physically identical provided the ease of forming the association product of the target nucleic acid molecule, the first nucleic acid probe and the second nucleic acid probe, and the ease of forming an association product consisting of a nucleic acid molecule other than the target nucleic acid molecule, the first nucleic acid probe and the second nucleic acid probe, are substantially the same when forming the three-component association product in (c) and when forming covalent bonds in (d). For example, in the case the temperature of a sample solution during formation of the three-component association product in (c) is within ±3° C. of the Tm value, then there are cases in which the temperature of the sample solution during formation of covalent bonds in (d) is also within ±3° C. of the Tm value. This is because, depending on the type of base sequence of the target nucleic acid molecule, specific association conditions are satisfied if the temperature is within ±3° C. of the Tm value, and even if there is a certain degree of fluctuation within the aforementioned temperature range, there is thought to be hardly any effect on the specificity of association product formation.

In the present embodiment, covalent bonds may be formed by a photochemical reaction. A photochemical reaction refers to a reaction that is carried out by radiating light of a specific wavelength and then utilizing that light energy. Since a method that forms covalent bonds by a photochemical reaction is able to form covalent bonds between nucleic acid strands of an association product by irradiating a sample solution with light of a specific wavelength, it is not necessary to vary conditions such as the composition of the aforementioned sample solution. Consequently, effects on the association product in the sample solution other than the formation of covalent bonds can be suppressed and the procedure is simple.

For example, by using a first nucleic probe in which at least one base in a region of the first nucleic acid probe that hybridizes with a target nucleic acid molecule is substituted with a photoreactive base derivative, and a second nucleic acid probe in which at least one base in a region of the second nucleic acid probe that hybridizes with a target nucleic acid molecule is substituted with a photoreactive base derivative, covalent bonds mediated by the aforementioned photoreactive base derivative can be formed between the target nucleic acid molecule and the first nucleic acid probe and between the target nucleic acid and the second nucleic acid probe by a photochemical reaction.

There are no particular limitations on the bases substituted with photoreactive base derivatives in the first nucleic acid probe and the second nucleic acid probe provided they are bases in regions that hybridize with the target nucleic acid molecule. In addition, only one base may be substituted with a photoreactive base derivative or two or more bases may be substituted with photoreactive base derivatives.

Here, a photoreactive base derivative refers to a base derivative that has a site at which the reactivity of an organic synthesis reaction (photoreactive site) is activated as a result of being irradiated with light of a specific wavelength, and is able to form a nucleic acid chain in the same manner as a naturally-occurring nucleotide.

An example of such a photoreactive base derivative is 3-cyanovinylcarbazole nucleoside ($^{CNV}K$) (see, for example, Non-Patent Document 2 or Non-Patent Document 3). Furthermore, a nucleic acid probe in which a base has been substituted with a photoreactive base derivative can be produced by using an unsubstituted nucleic acid probe as a raw material when, for example, synthesizing a nucleic acid probe using a known oligonucleotide synthesizer. In addition, after having produced an unsubstituted nucleic acid probe, a substituted nucleic acid probe can be obtained by introducing a suitable photoreactive functional group into a base that composes the nucleic acid probe by a known organic synthesis reaction.

More specifically, in the case of using $^{CNV}K$ for the photoreactive base derivative, after having formed a three-component association product composed of a target nucleic acid molecule, a first nucleic acid probe and a second nucleic acid probe in a sample solution in which they are contained, when the sample solution is irradiated with ultraviolet light containing light of 300 nm to 380 nm, light of 340 nm to 380 nm, light of 360 nm to 370 nm, or light of 366 nm, covalent bonds are formed between atoms that compose the pyrimidine base in the target nucleic acid molecule that forms a base pair with a purine base adjacent to the 5'-side of $^{CNV}K$ and atoms that compose $^{CNV}K$.

In addition, a photoreactive base derivative obtained by adding psoralen to thymine (T) or adenine (A) through a linker (see, for example, Proc. Natl. Acad. Sci. USA, Vol. 88, pp. 5602-5606, July 1991) may also be used. For example, in the case a TA sequence is present in the regions of a first nucleic acid probe and second nucleic acid probe that hybridize with a target nucleic acid molecule, a psoralen-bound nucleic acid probe is prepared in which psoralen is bound to the T or A in the aforementioned TA sequence through a linker. Next, after allowing the psoralen-bound nucleic acid probe and target nucleic acid molecule to associate, when irradiated with near ultraviolet light of 300 nm and the like, the first nucleic acid probe or the second nucleic acid probe that forms a base pair through this psoralen is crosslinked with the target nucleic acid molecule, thereby stabilizing the three-component association product.

Following (d), in (e), a solid phase carrier provided with a site that binds with a second marker is first added to the aforementioned sample solution, and the solid phase carrier and the three-component association product are bound through the second marker in the three-component association product. Subsequently, the three-component association product bound to the solid phase carrier is recovered by solid-liquid separation treatment.

The solid phase carrier used in the present embodiment is provided with a site that binds with a second marker. More specifically, the solid phase carrier is a solid phase carrier having on the surface thereof a substance that specifically or non-specifically binds or absorbs to the second marker. In the case the second marker is an oligonucleotide, examples of the aforementioned substance include an oligonucleotide that hybridizes with the aforementioned oligonucleotide, an antigen or antibody to the second marker, a ligand or receptor for the second marker, and a substance that specifically binds with the second marker in the manner of biotin and avidin. Furthermore, although the solid phase carrier may non-specifically bind to the second marker, it may bind specifically from the viewpoint of greater accuracy in detecting or quantifying target nucleic acid molecules.

There are no particular limitations on the method used to bind the substance that specifically or non-specifically binds or adsorbs to the second marker, and may be physically adsorbed or chemically bound to a functional group on the surface of the solid phase carrier. In the case of chemical bonding, the aforementioned substance can be bound by a method suitable for each functional group. Examples thereof include a reaction in which 1-ethyl-3-(3-dimethylaminopropyl)carbodiimide hydrochloride (EDAC), a reaction in which 1-ethyl-3-(3-dimethylaminopropyl)carbodiimido hydrochloride (EDC) and N-hydroxysuccinimide (NHS) are mixed in advance followed by bonding between carboxylic acid and an amino group, a reaction in which amino groups are crosslinked using a bipolar linker, and a reaction in which an activated aldehyde group or tosyl group bonds with a functional group in the substance that specifically or non-specifically binds or adheres to the second marker. A functional group may be preliminarily coated on the surface of the solid phase carrier in the case the surface of the solid phase carrier does not have a functional group.

There are no particular limitations on the shape or material and so forth of the solid phase carrier provided it is a solid provided with a site that binds with the second marker. For example, it may be a particle such as a bead that can be suspended in water and can be separated from a liquid by a common solid-liquid separation procedure, or a membrane, container or chip substrate. Specific examples of solid phase carriers include magnetic beads, silica beads, agarose gel beads, polyacrylamide resin beads, latex beads, plastic beads, ceramic beads, zirconia beads, silica membranes, silica filters and plastic plates. For example, in the case the solid phase carrier consists of particles such as beads, the aforementioned solid phase carrier is added to the aforementioned sample solution. In addition, in the case the solid phase carrier consists of a membrane or filter, the sample solution is passed through the solid phase carrier. In the case the solid phase carrier is a container coated with a substance that binds with the second marker on the inner walls thereof, the sample solution is injected into the container serving as the solid phase carrier.

For example, in the case the second marker is biotin, beads or filter having avidin or streptavidin bound to the surface thereof can be used as a solid phase carrier. In addition, in the case the second marker is digoxigenin (Dig), beads or filter having anti-Dig antibody bound to the surface thereof can be used as a solid phase carrier.

The aforementioned three-component association product is allowed to bind to the solid phase carrier through the second marker in the three-component association product by contacting the solid phase carrier with a sample solution containing the three-component association product. As a result of subsequently carrying out a solid-liquid separation procedure, the three-component association product bound to the solid phase carrier can be separated from the free first nucleic acid probe present in the liquid phase and recovered.

There are no particular limitations on the solid-liquid separation procedure provided it is a method that allows separation and recovery of the solid phase carrier in solution from a liquid component, and can be suitably selected and used from among known treatments used for solid-liquid separation treatment. For example, in the case the solid phase carrier consists of particles such as beads, a suspension containing the solid phase carrier may be subjected to centrifugal separation treatment to precipitate the solid phase carrier followed by removal of the supernatant, or the aforementioned solution may be filtered using a filter followed by recovering the solid phase carrier remaining on the surface of the filter paper. In addition, in the case the solid phase carrier consists of magnetic beads, a magnet may be brought in close proximity to a container containing the aforementioned solution to cause the solid phase carrier to converge at the surface of the container closest to the magnet followed by removing the supernatant. In the case the solid phase carrier is a container having an inner wall coated with a substance that binds to the second marker, liquid inside the container serving as the solid phase carrier is discarded. Furthermore, in the case the solid phase carrier is a membrane or filter, binding between the solid phase carrier and three-component association product and separation and recovery of the three-component association product bound to the solid phase carrier from the free first nucleic acid probe can be carried out in a single procedure by passing the aforementioned sample solution through the aforementioned solid phase carrier.

In the present embodiment, a solid phase carrier provided with a site that binds with a second marker is preliminarily added to a sample solution together with a nucleic acid-containing sample, a first nucleic acid probe and a second nucleic acid probe in (a), and in (c), after having formed a three-component association product bound to the solid phase carrier, the three-component association product bound to the solid phase carrier may be separated and recovered from the free first nucleic acid probe by solid-liquid separation treatment. In addition, after having prepared a sample solution obtained by adding a second marker preliminarily bound to a solid phase carrier, a nucleic acid-containing sample and a first nucleic acid probe in (a), and forming a three-component association product bound to the solid phase carrier in (c), the three-component association product bound to the solid phase carrier may be separated and recovered from the free first nucleic acid probe by solid-liquid separation treatment. Furthermore, the second marker used at this time may be reversibly or irreversibly bound to the solid phase carrier.

A solution containing the three-component association product bound to the solid phase carrier is prepared by adding a suitable solvent to the recovered solid phase carrier. The recovered solid phase carrier is supplied to (f) in the form of a solution in which it is contained therein. There are no particular limitations on the aforementioned solvent provided it is a solvent that does not hinder detection of light released from the first marker in a subsequent, and can be suitably selected and used from among buffers commonly used in the art. Examples of the aforementioned buffers include phosphate buffers and Tris buffers, such as phosphate-buffered saline (PBS, pH 7.4).

The recovered solid phase carrier may be washed with a suitable solvent prior to (f). As a result of washing, the free first nucleic acid probe can be more completely separated and removed from the three-component association product bound to the solid phase carrier. There are no particular limitations on the solvent used to wash the solid phase carrier provided it does not impair binding between the second marker and the solid phase carrier, and may be the same as or different from the buffer used to prepare the solution containing the three-component association product bound to the solid phase carrier supplied to (f).

In the case of carrying out solid-liquid separation treatment at room temperature and the like, non-specific association products (association products formed by non-specific hybridization) are formed easily. Consequently, in the present embodiment, the solid phase carrier may be washed in a state in which the formation of non-specific association products (such as association products with the second nucleic acid probe) by the first nucleic acid probe is suppressed.

For example, the solid phase carrier is washed with a solvent having a salt concentration such that the Tm value of the first nucleic acid probe is extremely low.

The solid phase carrier may be washed with a solvent having a salt concentration such that the Tm value of the first nucleic acid probe is lower than the temperature during washing. Although salt concentration varies according to the base sequence of the probe, when considering washing at a room temperature of about 25° C., a solvent may be used for washing that has a salt concentration such that the Tm value of the first nucleic acid probe is 25° C. or lower. Specific examples of the aforementioned solvent include solutions having a low salt concentration used during washing in a hybridization method, such as solutions having salt concentration of ×0.01 SSC (1.5 mM NaCl or 0.15 mM sodium citrate solution) or lower. The aforementioned solvent may also be a solvent that does not contain salt such as water. Washing with a highly stringent solution makes it possible to suppress the formation of non-specific association products and effectively remove the free first nucleic acid probe. In the present embodiment, since a target nucleic acid molecule, first nucleic acid probe and second nucleic acid probe are covalently bound, the three-component association product can be stably maintained even if washed under highly stringent conditions.

Subsequently, the first marker is released from the recovered three-component association product in (f).

There are no particular limitations on the method used to release the first marker provided it is a method that separates the first marker in the three-component association product from the solid phase carrier.

For example, the first marker can be released by adding a nucleolytic enzyme to the solution containing the three-component association product bound to the solid phase carrier and decomposing the first nucleic acid probe and other nucleic acid molecules with the aforementioned enzyme (f2). There are no particular limitations on the nucleolytic enzyme used to release the first marker, and may be a DNA nucleolytic enzyme, RNA nucleolytic enzyme or restrictase. Examples of DNA nucleolytic enzymes include S1 nuclease, mung bean nuclease, BAL 31 nuclease, exonuclease I, exonuclease III and DNase I etc. Examples of RNA nucleolytic enzymes include ribonuclease H etc., while examples of DNA/RNA nucleolytic enzymes include micrococcal nuclease etc.

The first nucleic acid probe or the second nucleic acid probe may be designed so as to contain a restrictase recognition sequence corresponding to a restrictase within the region in the first nucleic acid probe or second nucleic acid probe that hybridizes with the target nucleic acid molecule. In this case, the first marker can be separated from the solid phase carrier by digesting the restrictase recognition site in the three-component association product by restrictase treatment. Examples of restrictases include, but are not limited to, EcoRI and HindIII etc.

In addition, the first marker can also be released by chemically decomposing the first nucleic acid probe and other nucleic acid molecules with an alkali instead of by an enzymatic reaction (f4). More specifically, after adding a base to a solution containing the three-component association product bound to the solid phase carrier to make the pH of the solution alkaline, the solution is heated to 50° C. to 100° C., 70° C. to 100° C. or 80° C. to 100° C. Alkaline treatment is carried out at a pH and concentration at which the nucleic acid molecules decompose. In addition, there are no particular limitations on the type of base used, and may be an inorganic base or organic base. For example, a strongly basic solution such as a 0.1 mM sodium hydroxide solution or 0.1 mM potassium hydroxide solution is added to raise the pH of the solution containing the three-component association product bound to the solid phase carrier to pH 10 or higher, or pH 12 or higher, followed by heating to 50° C. or higher, or 70° C. or higher.

In addition, covalent bonds formed by a photochemical reaction using $^{CNV}K$ have been recently determined to be easily broken by intense energy. The energy applied at this time may be light energy, or heat energy.

Therefore, in the case of covalently bonding the first nucleic acid probe, the second nucleic acid probe and the target nucleic acid molecule by a photochemical reaction using $^{CNV}K$ as a photoreactive base derivative, the first marker can be released by irradiating the three-component association product bound to the solid phase carrier with ultraviolet light at 300 nm to 380 nm, or 340 nm to 380 nm under dissociating conditions (f1).

Here, dissociating conditions refer to conditions under which the target nucleic acid molecule and the first nucleic acid probe or the target nucleic acid molecule and the second nucleic acid probe dissociate in the case of not forming covalent bonds between the target nucleic acid molecule and the first nucleic acid probe or between the target nucleic acid molecule and the second nucleic acid probe. An example of dissociating conditions consists of low salt concentration conditions such that the Tm value of the first nucleic acid probe is extremely low in the same manner as washing treatment. More specifically, after having added the three-component association product bound to the solid phase carrier to, for example, a solution having a salt concentration such that the Tm value of the first nucleic acid probe is 25° C. or lower (which may also be a solution not containing salt such as water), the solution is irradiated with ultraviolet light at 300 nm to 380 nm.

In addition, in the case of covalently bonding the first nucleic acid probe, the second nucleic acid probe and the target nucleic acid molecule by a photochemical reaction using $^{CNV}K$ as a photoreactive base derivative, the first marker can also be released by heating the three-component association product bound to the solid phase carrier to a temperature sufficiently higher than the Tm value of the first nucleic acid probe. More specifically, the three-component association product bound to the solid phase carrier is heated to 80° C. or higher (f3). The three-component association product bound to the solid phase carrier may be heated after having added thereto a solvent such as water that does not impair detection of light released from the first marker.

Subsequently, in (g), the target nucleic acid molecule is detected by detecting the free first marker. A single molecule of the first marker is released from a single molecule of the three-component association product. Consequently, the number of first markers detected in (g) is theoretically equal to the number of target nucleic acid molecules in the nucleic acid-containing sample added in (a).

The free first marker can be detected by irradiating with light of an optimum wavelength in terms of the optical properties thereof and detecting the optical properties of light emitted from the aforementioned marker. Furthermore, detecting the optical properties of the marker refers to detecting an optical signal of a specific wavelength emitted from the aforementioned marker. Examples of the aforementioned signal include fluorescence intensity and fluorescence polarization.

There are no particular limitations on the method used to detect the first marker provided it is a method that enables detection and analysis of the intensity of fluorescent signals of molecules present in the solution or chronological changes (fluctuations) thereof. For example, the fluorescence intensity emitted from all fluorescent molecules in the solution may be measured or fluorescence intensity may be measured for each molecule.

The fluorescence intensity of a solution can be measured in accordance with ordinary methods using a fluorescence plate reader or other type of fluorescence spectrophotometer. The fluorescence intensity of a solution is dependent upon the amount of the first marker contained in the aforementioned solution. Consequently, by preliminarily preparing a calibration curve indicating the relationship between the content of the first marker and fluorescence intensity, the amount of the first marker in the solution, namely the amount of target nucleic acid molecules in the nucleic acid-containing sample, can be quantified.

Examples of methods used to measure fluorescence intensity for each molecule in a sample solution include fluorescence correlation spectroscopy (FCS) and fluorescence intensity distribution analysis (FIDA). Furthermore, detection and analysis of chronological changes in fluorescence signals of such molecules can be carried out in accordance with ordinary methods using, for example, a known single molecule fluorescence analysis system such as the MF20 Single Molecule Fluorescence Spectroscopy System (Olympus Corp.).

For example, a target nucleic acid molecule can be detected and analyzed by FIDA by detecting fluctuations in fluorescence intensity of a molecule present in the focused region of a confocal optical system, followed by calculating the number of molecules of the free first marker by carrying out statistical analyses.

In addition, a target nucleic acid molecule can be detected and analyzed by FCS by detecting fluctuations in fluorescence intensity of a molecule present in the focused region of a confocal optical system, followed by calculating the number of molecules of the free first marker by carrying out statistical analyses.

In the method for detecting a target nucleic acid molecule of the present embodiment, a fluorescent molecule in a solution can also be detected according to the scanning molecule counting method. More specifically, by moving the location of a photodetection region of an optical system of a confocal microscope or multi-photon microscope in a measurement sample solution using that optical system while detecting fluorescent light from the aforementioned photodetection region, the number of molecules of the free first marker present in the measurement sample solution can be calculated (see, for example, International Publication No. WO 11/108,369, International Publication No. WO 11/108,370 and International Publication No. WO 11/108,371).

The scanning molecule counting method is a technology that enables counting of particles that emit light (luminescent particles) in a measurement sample solution, or acquisition of information relating to concentration or number density of luminescent particles in a measurement sample solution, by detecting light emitted from the luminescent particles in a microregion when the luminescent particles are dispersed and move about randomly in the measurement sample solution while scanning the interior of the sample solution with the microregion. In this method, the amount of sample required for measurement is extremely small (such as roughly several tens of microliters) and measurement time is short in the same manner as optical analysis technologies such as FIDA, while also enabling quantitative detection of the concentration, number density or other properties of luminescent particles at a lower concentration or number density in comparison with the case of using an optical analysis technology such as FIDA.

In the present embodiment, the "photodetection region" of a confocal microscope or multi-photon microscope refers to a microregion in which light is detected in those microscopes, and in the case illumination light is imparted from an object lens, the region where that illumination light is focused corresponds to a microregion. Furthermore, this microregion is defined by the positional relationship between the object lens and pinhole in a confocal microscope in particular.

Since the photodetection mechanism per se of the scanning molecule counting method is composed so as to detect light from a photodetection region of a confocal microscope or multi-photon microscope in the same manner as in the case of optical analysis technologies such as FIDA, the amount of sample solution is similarly extremely small. However, since statistical processing such as calculating fluctuations in fluorescence intensity are not performed in the scanning molecule counting method, the optical analysis technology of the scanning molecule counting method can be applied to samples solutions in which particle number density or concentration is much lower than the level required by optical analysis technologies such as FIDA.

In addition, since the scanning molecule counting method detects individual particles dispersed or dissolved in a solution, counting of particles, determination of particle concentration or number density in a measurement sample solution, or acquisition of information relating to concentration or number density, can be carried out quantitatively using that information. Namely, according to the scanning molecule counting method, since particles are detected one at a time by creating a 1:1 correlation between a particle passing through a photodetection region and a detected optical signal, particles dispersed and moving randomly in a solution can be counted. Consequently, the concentration or number density of particles in a measurement sample solution can be determined more accurately than in the past. For example, in the case of carrying out detection of the free first marker in the method for detecting a target nucleic acid molecule of the present embodiment according to the scanning molecule counting method, individually detecting particles in a measurement sample solution according to the light emitted by a first marker, and then counting the number thereof and determining particle concentration, the first marker can be detected even if the concentration of the first marker in the measurement sample solution is even lower than the concentration able to be determined based on fluorescence intensity as measured with a fluorescence spectrophotometer or plate reader. Use of the scanning molecule counting method enables target nucleic acid molecules to be quantitatively detected without having to amplify in advance even in the case the concentration of the target nucleic acid molecules in the nucleic acid-containing sample is extremely low and the concentration of the free first marker is 1 femtomole or less.

Moreover, according to an aspect in which the interior of a measurement sample solution is scanned with a photodetection region by changing the light path of the optical system, the interior of the measurement sample solution can be observed uniformly or the measurement sample solution can be observed in a mechanically stable state without imparting mechanical vibrations or actions attributable to fluid dynamics to the measurement sample solution. Consequently, for example, the reliability of quantitative detection results is improved in comparison with the case of causing the generation of flow in a sample, and measurements can be carried out in the absence of effects caused by dynamic action or artifacts on particles to be detected in the measurement sample solution (the free first marker in the present invention). In the case of imparting flow to a sample, in addition to it being difficult to impart a uniform flow at all times, the configuration of the device becomes complex. In addition, together with causing a considerable increase in the amount of sample required, particles in solution, a luminescent probe, a complex thereof or other substances may undergo deterioration or degeneration due to the fluid dynamic action generated by that flow.

In the case of highly sensitive measurement such as when measuring single molecules, and particularly in the scanning molecule counting method, there are cases in which there is a decrease in the detection accuracy of luminescent particles having a comparatively slow diffusional mobility in a solution in the manner of a solid phase carrier and the like. In the present embodiment, as a result of targeting detection on the first marker in a free state separated from a solid phase carrier, the effects of the solid phase carrier can be eliminated and the first marker can be detected with high accuracy even in the case of using a fluorescent single molecule measurement method.

FIG. 1 is a drawing schematically showing one aspect of the method for detecting a target nucleic acid molecule of the present embodiment. In FIG. 1, a fluorescent substance is used for the first marker, biotin is used for the second marker, and avidin beads (beads coated with avidin on the surface thereof) are used for the solid phase carrier. Covalent bonds (crosslinks) are formed by a photochemical reaction using $^{CNV}K$ between the first nucleic acid probe and the target nucleic acid molecule and between the second nucleic acid probe and the target nucleic acid molecule, and the first marker is released using a nucleolytic enzyme.

First, a three-component association product formed by hybridization of a target nucleic acid molecule 1, a first nucleic acid probe 2 having a fluorescent substance 2a bound thereto, and a second nucleic acid probe 3 having biotin 3a bound thereto is irradiated with ultraviolet light at 365 nm to respectively form covalent bonds (crosslinks) between $^{CNV}K$ 2b in the first nucleic acid probe 2 and the target nucleic acid molecule 1 and between $^{CNV}K$ 3b in the second nucleic acid probe 3 and the target nucleic acid molecule 1 (first illustration in FIG. 1). Avidin beads 4 are added to the sample solution after crosslinking and the three-component association product is bound to the avidin beads 4 through the biotin 3a (second illustration in FIG. 1). Subsequently, after washing with a low salt concentration solution, the target nucleic acid molecule 1, the first nucleic acid probe 2 and the second nucleic acid probe 3 are decomposed by treating with a nucleolytic enzyme (third illustration in FIG. 1), and the fluorescent substance 2a is released from the avidin beads 4 (fourth illustration in FIG. 1).

In addition, in the case of enabling the second nucleic acid probe to hybridize with the target nucleic acid molecule in the solid-liquid separation treatment of (e) and the washing treatment prior thereto as well by making the Tm value of the association product of the second nucleic acid probe and the target nucleic acid molecule to be sufficiently higher than the Tm value of the association product of the first nucleic acid probe and the target nucleic acid molecule, at least one covalent bond is formed only between the first nucleic acid probe and the target nucleic acid molecule. Even in the case of not forming a covalent bond between the second nucleic acid probe and the target nucleic acid molecule, the target nucleic acid molecule can be detected without being affected by free labeled probe or solid phase carrier in the same manner as the method for detecting a target nucleic acid molecule of the present embodiment.

For example, by making the Tm value of the association product of the first nucleic acid probe and the target nucleic acid molecule to be lower, and specifically 10° C. or more lower, than the temperature of the washing solution used in the aforementioned washing treatment, and making the Tm value of the association product of the second nucleic acid probe and the target nucleic acid molecule to be higher, and specifically 10° C. or more higher, than the temperature of the washing solution, the free first nucleic acid probe can be removed by the aforementioned washing treatment.

An example of a method used to make the Tm value of the association product of the second nucleic acid probe and the target nucleic acid molecule higher than the Tm value of the association product of the first nucleic acid probe and the target nucleic acid molecule consists of composing the second nucleic acid probe so as to contain in at least a portion thereof a nucleic acid-like substance capable of forming a stronger base pair than a naturally-occurring oligonucleotide such as PNA, and composing the nucleic acid chain portion of the first nucleic acid probe with only a naturally-occurring oligonucleotide. As a result of carrying out operations (a) to (g) in the same manner as the method for detecting a target nucleic acid molecule of the present embodiment as previously described, with the exception of carrying out the solid-liquid separation treatment of (e) and washing treatment prior thereto using these nucleic acid probes under conditions such that a first nucleic acid probe that non-specifically hybridizes with other nucleic acid molecules can be released without forming a covalent bond with the target nucleic acid molecule and the second nucleic acid probe is able to hybridize with the target nucleic acid molecule, the first nucleic acid probe that has formed an association product with the target nucleic acid molecule can be detected in a state in which the first nucleic acid probe that has not formed a covalent bond with the target nucleic acid molecule is removed. In this case, release of the aforementioned first marker from the three-component association product recovered in the aforementioned (f) can be carried out by washing the three-component association product bound to the solid phase carrier under highly stringent solution conditions to the extent that the second nucleic acid probe is unable to hybridize with the target nucleic acid molecule. The first marker forming an association product with the target nucleic acid molecule is released from the solid phase carrier as a result of the second nucleic acid probe bound to the solid phase carrier dissociating from the target nucleic acid molecule.

<Target Nucleic Acid Molecule Detection Kit>

Various reagents and instruments, including the first nucleic acid probe and the second nucleic acid probe, used in the method for detecting a target nucleic acid molecule of the present embodiment may also be incorporated in a kit. The aforementioned kit allows the method for detecting a target nucleic acid molecule of the present invention to be carried out easily. In addition to the aforementioned nucleic acid probes, a solid phase carrier provided with a site that binds to a second marker, various buffers used to prepare sample solutions, a washing solution for washing the three-component association product after stabilizing with covalent bonds, and an incubator equipped with a constant temperature device, can be included in the aforementioned kit.

EXAMPLES

Although the following provides a more detailed explanation of the present invention by indicating examples thereof, the aspects of the present invention are not limited to the following examples.

Example 1

Unlabeled target nucleic acid molecules were detected according to the method for detecting a target nucleic acid molecule of one aspect of the present invention by using, as the target nucleic acid molecule, a single-stranded RNA having a sequence homologous with human microRNA in the form of let-7a (hsa-let-7a, 5'-UGAGGUAGUAGGUU-GUAUAGUU-3')(SEQ ID NO: 1).

A nucleic acid probe (7a right tamra-1,5'-ACTAKCTCA-3')(SEQ ID NO: 4) having a base sequence complementary to the region of let-7a from the 5'-terminal to the 9th base, and obtained by substituting a base complementary to the 5th base from the 5'-terminal of let-7a with a crosslinking base derivative in the form of $^{CNV}K$ and binding a first marker in the form of the fluorescent substance TAMRA to the 3'-terminal, was used as the first nucleic acid probe. In addition, a nucleic acid probe (B-7aL1,5'-TTTTTTTTT-TAACTAKACAACCT-3')(SEQ ID NO: 5) having a base sequence complementary to the region of let-7a from the 3'-terminal to the 13th base on the 3-terminal side, and obtained by substituting a base complementary to the 6th base from the 3'-terminal of let-7a with a crosslinking base derivative in the form of $^{CNV}K$, and adding a second marker in the form of ten thymidine bases and biotin to the 5'-terminal side, was used as the second nucleic acid probe. In each of the base sequences, "K" refers to $^{CNV}K$. In addition, the base sequences of each probe prior to substitution with $^{CNV}K$ are shown in SEQ ID NO: 2 and SEQ ID NO: 3. Furthermore, the first nucleic acid probe and the second nucleic acid probe were synthesized by Fasmac Co., Ltd.

Solutions obtained by respectively adding the first nucleic acid probe and the second nucleic acid probe at a final concentration of 100 nM, and respectively adding a target nucleic acid molecule in the form of synthetic RNA composed of abase sequence complementary to let-7a at final concentrations of 10 nM, 1 nM, 100 pM, 10 pM, 1 pM and 0 pM were prepared in 50 µl aliquots for use as sample solutions (150 mM NaCl, 10 mM Tris-HCl, 0.1% Tween 20). An RNAase inhibitor (trade name: SUPERase In, Ambion Corp.) was added to each solution at a concentration of 0.1 U/µL. Furthermore, the aforementioned target nucleic acid molecule used was synthesized by Hokkaido System Science Co., Ltd.

Each sample solution was denatured for 2 minutes at 70° C. followed by carrying out hybridization (association) by lowering the temperature to 10° C. at the rate of 1° C./15 seconds. Subsequently, the sample solutions were irradiated with ultraviolet light at 365 nm while cooling in ice. 10 µL of magnetic beads in the form of Dynabeads (trade name:

Dynabeads MyOne Streptavidin, Invitron Ltd.) were added to each sample solution followed by incubating for 15 minutes at room temperature. Subsequently, the magnetic beads were washed once each with ×1 SSC, ×0.1 SSC and ×0.01 SSC. Following washing, 20 μL aliquots of S1 nuclease solution at a concentration of 10 units/20 μL (Takara Bio Inc.) were added and allowed to react for 10 minutes at 23° C. After adding 30 μL of TE buffer to the reaction solutions, the supernatant was recovered after collecting the magnetic beads on the side of the container and then irradiated with light at the excitation wavelength of TAMRA followed by measurement of the supernatant by fluorescence intensity distribution analysis (FIDA).

Figure 2:
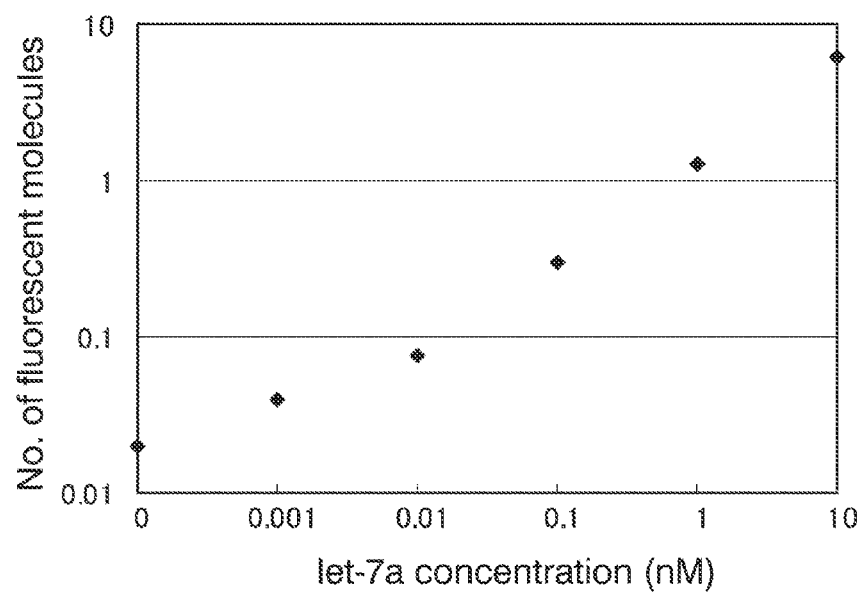
FIG. 2 is a drawing showing the results of using the FIDA method to measure the number of molecules of the fluorescent substance TAMRA released from magnetic beads recovered from various sample solutions by a nucleolytic enzyme reaction in Example 1.

The results of using FIDA to measure the number of molecules of the fluorescent substance TAMRA released from the magnetic beads recovered from each sample solution by a nucleolytic enzyme reaction are shown in FIG. 2. Target nucleic acid molecule concentration (nM) is plotted on the horizontal axis, while the number of fluorescent molecules is plotted on the vertical axis. As a result of measurement, the number of fluorescent molecules was determined to decrease concentration-dependently from 10 nM to 1 pM. Fluorescent molecules were determined to be able to be detected at a concentration of 1 pM (50 attomol at 50 μL) in particular.

Example 2

The release of a first marker from a solid phase carrier was carried out in the method for detecting a target nucleic acid molecule in another aspect of the present invention by a nucleolytic enzyme reaction or irradiating with ultraviolet light under low salt concentration conditions.

First, samples solutions containing a target nucleic acid molecule, first nucleic acid probe and second nucleic acid probe were prepared in the same manner as Example 1 with the exception of using, as the target nucleic acid molecule, a synthetic RNA composed of a base sequence homologous to let-7a at a final concentration of 10 nM or 0 nM, and after denaturing followed by hybridization (association), covalent bonds were formed by irradiating with ultraviolet light. 10 μL of magnetic beads in the form of Dynabeads (trade name: Dynabeads MyOne Streptavidin, Invitron Ltd.) were added to each sample solution followed by incubating for 15 minutes at room temperature. Subsequently, the magnetic beads were washed once each with ×1 SSC, ×0.1 SSC and ×0.01 SSC.

Following washing, 50 μL of ×0.1 SSC, ×0.01 SSC or pure water were added, and after heating for 1 minute at 50° C., the sample solutions were irradiated with ultraviolet light at 365 nm for 10 seconds while in that state. After collecting the magnetic beads on the side of the container, the supernatant was recovered and irradiated with light at the excitation wavelength of TAMRA followed by measuring the aforementioned supernatant by fluorescence correlation spectroscopy (FCS).

In addition, magnetic beads similarly bound with a three-component association product were washed once each with ×1 SSC, ×0.1 SSC and ×0.01 SSC, followed by adding S1 Nuclease solution (Takara Bio Inc.) in the same manner as Example 1 and allowing to react, adding 30 μL of TE buffer to the resulting reaction solutions, recovering the supernatant after collecting the magnetic beads on the side of the container, irradiating with light at the excitation wavelength of TAMRA, and measuring the aforementioned supernatant by fluorescence intensity distribution analysis (FIDA).

In addition, S1 Nuclease solution (Takara Bio Inc.) was added to washed magnetic beads and allowed to react in the same manner as Example 1 and 30 μL of TE buffer were added to the resulting reaction solution, followed by recovering the supernatant after collecting the magnetic beads on the side of the container, irradiating with light at the excitation wavelength of TAMRA, and measuring the aforementioned supernatant by fluorescence correlation spectroscopy (FCS) in the same manner as Example 1 with the exception of not adding a target nucleic acid molecule to the sample solution for use as a control.

Figure 3:
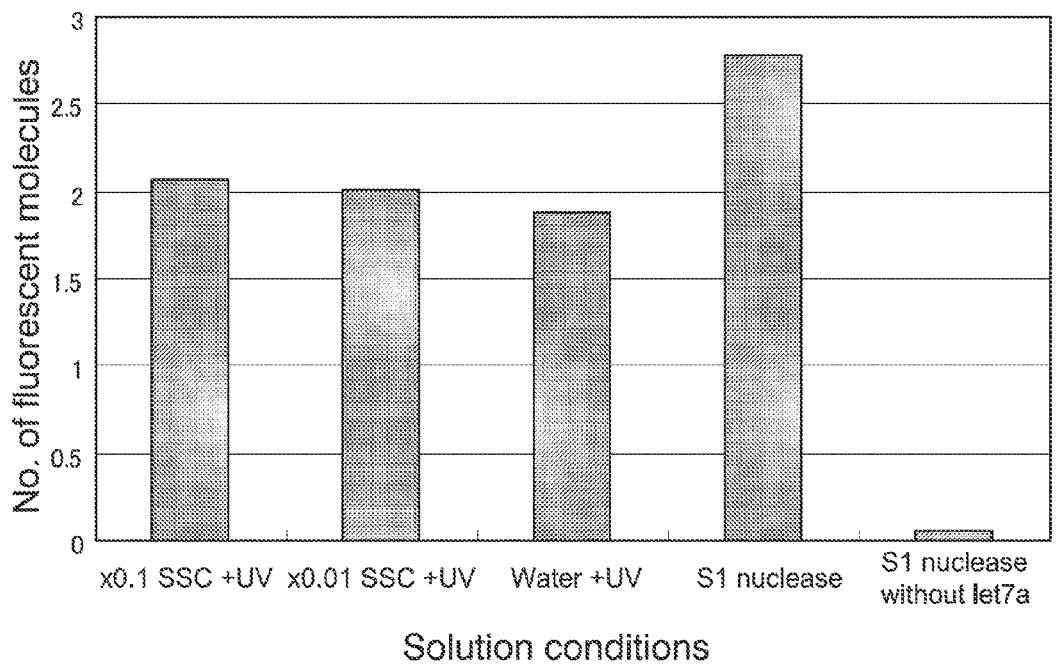
FIG. 3 is a drawing showing the results of using the FCS method to measure the number of molecules of the fluorescent substance TAMRA released from magnetic beads recovered from various sample solutions by a nucleolytic enzyme reaction or irradiating with ultraviolet light under low salt concentration conditions in Example 2.

The results of using FCS to measure the number of molecules of the fluorescent substance TAMRA released from the magnetic beads recovered from each sample solution are shown in FIG. 3. The treatment used to release TAMRA is plotted on the horizontal axis, while the number of fluorescent molecules analyzed using FCS is plotted on the vertical axis. In addition, in FIG. 3, "S1 nuclease without let-7a" indicates the results of the sample solution to which the target nucleic acid molecule was not added. Roughly two fluorescent molecules were able to be measured under the conditions of each solution, thereby clearly demonstrating that the first marker is released from the solid phase carrier by an enzyme reaction using a nucleolytic enzyme or by irradiating with ultraviolet light under low salt concentration conditions according to the method for detecting a target nucleic acid molecule in one aspect of the present invention.

Example 3

The release of a first marker from a solid phase carrier was carried out in the method for detecting a target nucleic acid molecule in still another aspect of the present invention by heating under alkaline conditions or heating under low salt concentration conditions.

First, samples solutions containing a target nucleic acid molecule, first nucleic acid probe and second nucleic acid probe were prepared in the same manner as Example 1 with the exception of using, as the target nucleic acid molecule, a synthetic RNA composed of a base sequence homologous to let-7a at a final concentration of 10 nM or 0 nM, and after denaturing followed by hybridization (association), covalent bonds were formed by irradiating with ultraviolet light. 10 μL of magnetic beads in the form of Dynabeads (trade name: Dynabeads MyOne Streptavidin, Invitron Ltd.) were added to each sample solution followed by incubating for 15 minutes at room temperature. Subsequently, the magnetic beads were washed once each with ×1 SSC, ×0.1 SSC and ×0.01 SSC.

Following washing, 50 μL of 10 mM NaOH, 1 mM NaOH or pure water were added, and after heating for 30 minutes at 70° C., 80° C. or 90° C., the sample solutions were irradiated with ultraviolet light at 365 nm for 10 seconds while in that state. After collecting the magnetic beads on the side of the container, the supernatant was irradiated with light at the excitation wavelength of TAMRA followed by measuring the aforementioned supernatant by fluorescence correlation spectroscopy (FCS).

Figure 4:
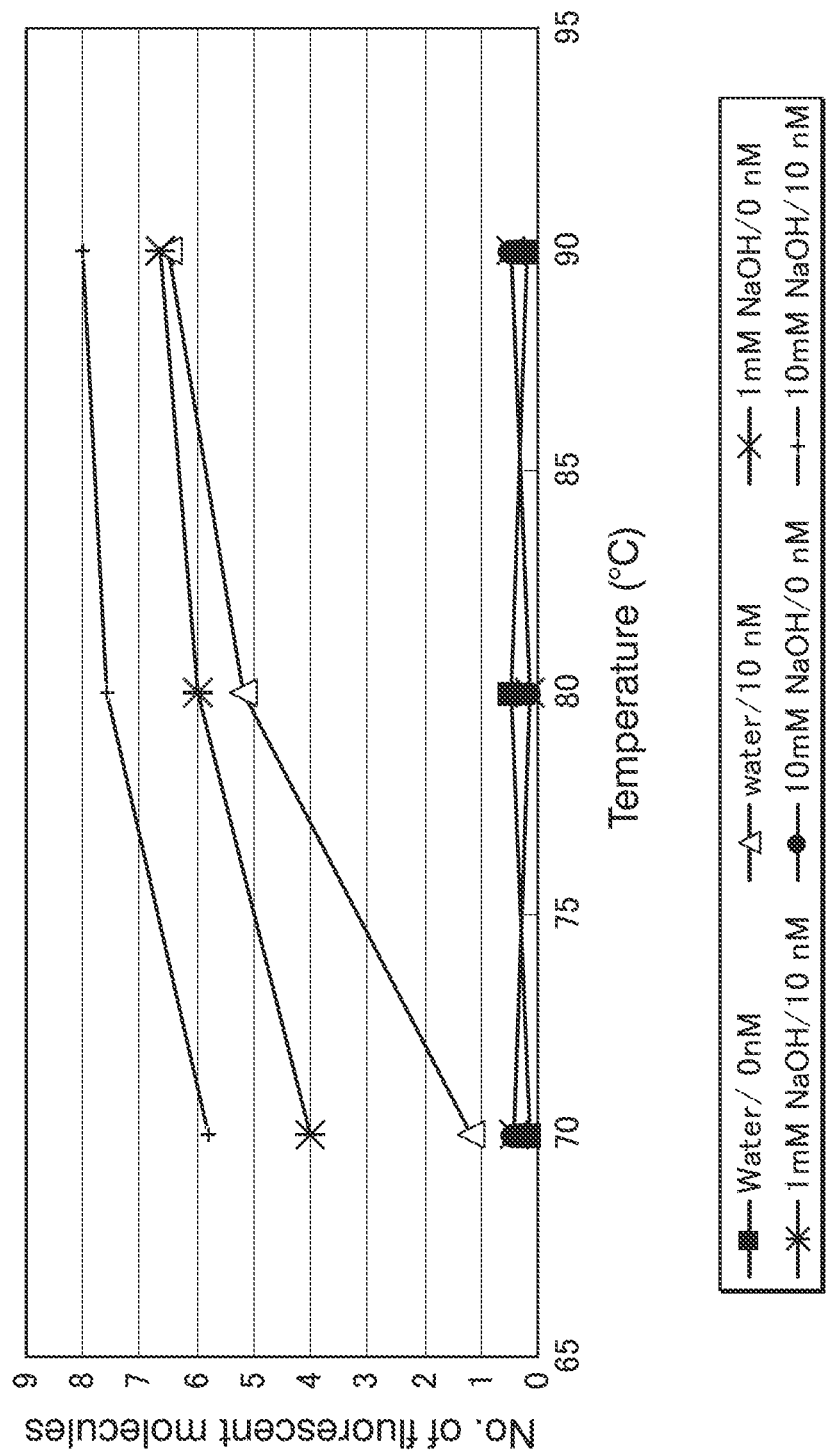
FIG. 4 is a drawing showing the results of using the FCS method to measure the number of molecules of the fluorescent substance TAMRA released from magnetic beads recovered from various sample solutions by heating under low salt concentration conditions or alkaline conditions in Example 3.

The results of using FCS to measure the number of molecules of the fluorescent substance TAMRA released from the magnetic beads recovered from each sample solution by heating under low salt concentration conditions or alkaline conditions are shown in FIG. 4. The temperature during release of TAMRA is plotted on the horizontal axis, while the number of fluorescent molecules analyzed using FCS is plotted on the vertical axis. In the legend of FIG. 4, "Water/0 nM" and "Water/10 nM" indicate results in the case of heating magnetic beads prepared from a sample solution having a target nucleic acid molecule concentration of 0 nM or 10 nM in water, "1 mM NaOH/0 nM" and "1 mM NaOH/10 nM" indicate results in the case of heating magnetic beads prepared from a sample solution having a target nucleic acid molecule concentration 0 nM or 10 nM in 1 mM NaOH, and "10 mM NaOH/0 nM" and "10 mM NaOH/10 nM" indicate results in the case of heating magnetic beads prepared from sample solution having a target nucleic acid molecule concentration of 0 nM or 10 nM in 10 mM NaOH. As a result, hardly any fluorescent molecules were detected at any of the temperatures from magnetic beads prepared from samples not containing target nucleic acid molecules (such as "Water/0 nM"). In addition, in the case of heating magnetic beads in NaOH, a higher concentration of NaOH was determined to result in the release of a larger amount of fluorescent dye, while treatment at 90° C. was determined to result in a larger number of free fluorescent molecules than that at 70° C. In this manner, even in the case of heating under alkaline conditions at 50° C. to 100° C., the first marker in the form of a fluorescent substance was determined to be able to be released from the solid phase carrier, thereby enabling highly sensitive measurement using a fluorescent single molecule measurement method in the manner of FCS.

On the other hand, in the case of heating magnetic beads in pure water, although hardly any fluorescent molecules (TAMRA) were detected at 70° C., release of TAMRA was able to be measured at 80° C. or higher, and at 90° C., fluorescent molecules were able to be measured at a concentration roughly equal to that of alkaline treatment, and it was determined that by heating at 80° C. or higher, or 90° C. or higher, the first marker in the form of a fluorescent substance was able to be released from the solid phase carrier even in pure water.

Example 4

The release of a first marker from a solid phase carrier was carried out by heating in the method for detecting a target nucleic acid molecule in still another aspect of the present invention.

First, samples solutions containing a target nucleic acid molecule, first nucleic acid probe and second nucleic acid probe were prepared in the same manner as Example 1 with the exception of using, as the target nucleic acid molecule, a synthetic RNA composed of a base sequence homologous to let-7a at a final concentration of 10 nM or 0 nM, and after denaturing followed by hybridization (association), covalent bonds were formed by irradiating with ultraviolet light. 10 µL of magnetic beads in the form of Dynabeads (trade name: Dynabeads MyOne Streptavidin, Invitron Ltd.) were added to diluted sample solutions obtained by diluting 10-fold with ×1B&W buffer (0.5 M NaCl, 5 mM Tris) and bringing to a total volume of 50 µL followed by incubating for 15 minutes at room temperature. Subsequently, the magnetic beads were washed once each with ×1 SSC, ×0.1 SSC and ×0.01 SSC.

Following washing, 50 µL of ×1 SSC, ×1 1TE (10 mM Tris, 1 mM EDTA) or pure water were added, and after heating for 30 minutes at 90° C., the magnetic beads were collected on the side of the container followed by measuring the aforementioned supernatant by fluorescence intensity distribution analysis (FIDA).

Figure 5:
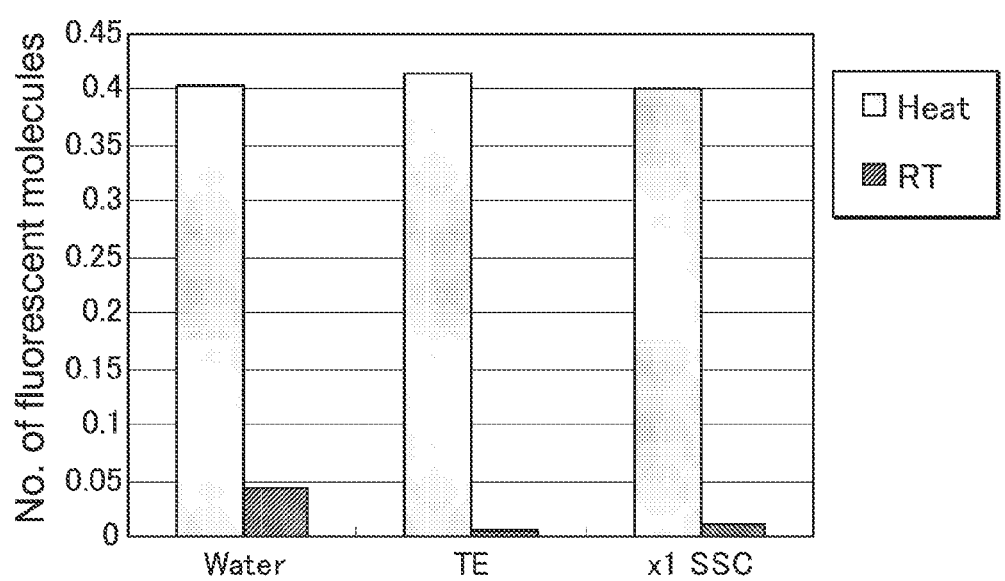
FIG. 5 is a drawing showing the results of using the FIDA method to measure the number of molecules of the fluorescent substance TAMRA released from magnetic beads recovered from various sample solutions by heating in Example 4.

The results of using FIDA to measure the number of molecules of the fluorescent substance TAMRA released from the magnetic beads recovered from each sample solution by heating are shown in FIG. 5. The solution conditions during heating are plotted on the horizontal axis, while the number of fluorescent molecules analyzed using FIDA is plotted on the vertical axis. In the legend of FIG. 5, "Heat" indicates results in the case of heating at 90° C., and "RT" indicates results in the case of not heating. In the case of not heating, hardly any fluorescent molecules were detected under all solution conditions. On the other hand, in the case of heating at 90° C., fluorescent molecules were detected under all conditions.

On the basis of these results, the release of fluorescent molecules was determined to be able to be detected without using alkaline treatment and the like by heating at 90° C.

In the method for detecting a target nucleic acid molecule according to the examples of the present invention, a target nucleic acid molecule bound to a labeled nucleic acid probe is separated and recovered from free labeled nucleic acid probe followed by measuring in the state of being separated from a solid phase carrier. Consequently, use of the method for detecting a target nucleic acid molecule in an aspect of the present invention makes it possible to detect target nucleic acid molecules with high accuracy without being affected by free labeled probe or a solid phase carrier.

BRIEF DESCRIPTION OF THE REFERENCE SYMBOLS

1: Target nucleic acid molecule, 2: first nucleic acid probe, 2a: fluorescent substance, 2b: $^{CNV}$K, 3: second nucleic acid probe, 3a: biotin, 3b: $^{CNV}$K, 4: avidin beads

The invention claimed is:

1. A method for detecting a target nucleic acid molecule in a nucleic acid-containing sample, comprising:
   (a) preparing a sample solution by adding said nucleic acid-containing sample, a first nucleic acid probe that has a first marker bound thereto and specifically hybridizes with a region of the target nucleic acid molecule, and a second nucleic acid probe that has a second marker bound thereto and specifically hybridizes with a region of the target nucleic acid molecule that differs from the region hybridized by the first nucleic acid probe, wherein the first marker is a luminescent substance;
   (b) denaturing the target nucleic acid molecule in the sample solution prepared in step (a);
   (c) allowing the target nucleic acid molecule, the first nucleic acid probe, and the second nucleic acid probe in the sample solution to associate each other after step (b);
   (d) forming at least one covalent bond between the target nucleic acid molecule and the first nucleic acid probe and forming at least one covalent bond between the target nucleic acid molecule and the second nucleic acid probe, thereby forming a three-component association product comprising the target nucleic acid molecule, the first nucleic acid probe and the second nucleic acid probe;
   (e) adding, after step (d), a solid phase carrier with a site that binds with the second marker to the sample solution such that the three-component association product binds to the solid phase carrier through the second marker in the three-component association product, recovering the three-component association product bound to the solid phase carrier by a solid-liquid separation procedure and forming a recovered three-component association product;
   (f) releasing the first marker from the recovered three-component association product after step (e); and
   (g) detecting the target nucleic acid molecule by detecting the first marker released from the recovered three-component association product after step (f).

2. The method according to claim 1, wherein
in step (f), the first marker is released from the three-component association product by:
   (f1) irradiating the three-component association product with an ultraviolet light at 300 nm to 380 nm under conditions in which the target nucleic acid molecule, the first nucleic acid probe and the second nucleic acid probe of the three-component association product dissociate each other if a covalent bond is not formed between the target nucleic acid molecule and the first nucleic acid probe or between the target nucleic acid molecule and the second nucleic acid probe;

(f2) decomposing the three-component association product with a nucleolytic enzyme;

(f3) heating the three-component association product to 80° C. or higher which is a temperature sufficiently higher than the melting temperature ($T_m$) value of the first nucleic acid probe; or, (f4) heating the three-component association product to 50° C. to 100° C. under alkaline conditions.

3. The method according to claim 2, wherein step (f1) is carried out in a solution containing a salt at a concentration at which the $T_m$ value of the first nucleic acid probe is 25° C. or lower.

4. The method according to claim 1, wherein each of the first nucleic acid probe and the second nucleic acid probe comprise a photoreactive base derivative, and
wherein the covalent bond between the target nucleic acid molecule and the first nucleic acid probe and the covalent bond between the target nucleic acid molecule and the second nucleic acid probe are formed by a photochemical reaction mediated by the photoreactive base derivative.

5. The method according to claim 4, wherein at least one base in a region of the first nucleic acid probe that hybridizes with the target nucleic acid molecule is substituted with a photoreactive base derivative, and at least one base in a region of the second nucleic acid probe that hybridizes with the target nucleic acid molecule is substituted with a photoreactive base derivative.

6. The method according to claim 4, wherein the photoreactive base derivative is 3-cyanovinylcarbazole nucleoside, and the covalent bond between the target nucleic acid molecule and the first nucleic acid probe and the covalent bond between the target nucleic acid molecule and the second nucleic acid probe are formed by irradiating the sample solution with a light at 340 nm to 380 nm in step d).

7. The method according to claim 1, wherein,
prior to step (f),
the three-component association product bound to the solid phase carrier recovered in step (e) is washed with a washing solution having a salt concentration at which the Tm value of the first nucleic acid probe is 25° C. or lower.

8. The method according to claim 1,
wherein the luminescent substance of the first nucleic acid probe produces a fluorescent signal, and
wherein, in step (g), said detecting the first marker released from the recovered three-component association product is carried out using a fluorescent single molecule measurement method.

9. The method according to claim 8, wherein the fluorescent single molecule measurement method comprises:
(h) calculating the number of molecules of the first marker released from the recovered three-component association product using fluorescence correlation spectroscopy or fluorescence intensity distribution analysis, or
(i) calculating the number of molecules of the first marker released from the recovered three-component association product using a confocal microscope or multiphoton microscope.

10. A method for detecting a target nucleic acid molecule in a nucleic acid-containing sample, comprising:
(a) preparing a sample solution obtained by adding said nucleic acid-containing sample, a first nucleic acid probe that has a first marker bound thereto and specifically hybridizes with a region of the target nucleic acid molecule, a second nucleic acid probe that has a second marker bound thereto and specifically hybridizes with a region of the target nucleic acid molecule that differs from the region hybridized by the first nucleic acid probe, and a solid phase carrier with a site that binds with the second marker, wherein the first marker is a luminescent substance;
(b) denaturing the target nucleic acid molecule in the sample solution prepared in step (a);
(c) allowing the target nucleic acid molecule, the first nucleic acid probe, and the second nucleic acid probe in the sample solution to associate each other after step (b);
(d) forming at least one covalent bond between the target nucleic acid molecule and the first nucleic acid probe and forming at least one covalent bond between the target nucleic acid molecule and the second nucleic acid probe, thereby forming a three-component association product bound to the solid phase carrier comprising the target nucleic acid molecule, the first nucleic acid probe and the second nucleic acid probe:
(e) recovering the three-component association product bound to the solid phase carrier by solid-liquid separation procedure and forming a recovered three-component association product;
(f) releasing the first marker from the recovered three-component association product after step (e); and
(g) detecting the target nucleic acid molecule by detecting the first marker released from the recovered three-component association product after step (f).

11. The method according to claim 10, wherein, in step (a), the second nucleic acid probe is bound to the solid phase carrier through the second marker.

* * * * *